(12) United States Patent
Wu et al.

(10) Patent No.: US 11,332,788 B2
(45) Date of Patent: *May 17, 2022

(54) SELF ASSEMBLED PATTERNING USING PATTERNED HYDROPHOBIC SURFACES

(71) Applicant: Illumina, Inc., San Diego, CA (US)

(72) Inventors: Yir-Shyuan Wu, Albany, CA (US); Yan-You Lin, Fremont, CA (US); M. Shane Bowen, San Diego, CA (US); Cyril Delattre, San Diego, CA (US); Fabien Abeille, Grenoble (FR); Tarun Khurana, Fremont, CA (US); Arnaud Rival, Grenoble (FR); Poorya Sabounchi, Atherton, CA (US); Dajun Yuan, San Diego, CA (US); Maria Candelaria Rogert Bacigalupo, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/153,379

(22) Filed: Jan. 20, 2021

(65) Prior Publication Data

US 2021/0139979 A1    May 13, 2021

Related U.S. Application Data

(63) Continuation of application No. 16/096,669, filed as application No. PCT/US2017/033169 on May 17, 2017, now Pat. No. 10,900,076.

(60) Provisional application No. 62/338,394, filed on May 18, 2016.

(51) Int. Cl.
| | | |
|---|---|---|
| *C12Q 1/6874* | (2018.01) | |
| *C12Q 1/6806* | (2018.01) | |
| *G03F 7/00* | (2006.01) | |
| *B05D 3/06* | (2006.01) | |
| *G03F 7/20* | (2006.01) | |

(52) U.S. Cl.
CPC .............. *C12Q 1/6874* (2013.01); *B05D 3/06* (2013.01); *C12Q 1/6806* (2013.01); *G03F 7/0002* (2013.01); *G03F 7/20* (2013.01)

(58) Field of Classification Search
CPC ...... B05D 3/06; C12Q 1/6806; C12Q 1/6874; G03F 7/20; G03F 7/2002
USPC ................................................ 430/18, 320
See application file for complete search history.

(56) References Cited

U.S. PATENT DOCUMENTS

| | | | |
|---|---|---|---|
| 7,794,799 B1 * | 9/2010 | Kim ....................... | B82Y 30/00 427/532 |
| 10,900,076 B2 * | 1/2021 | Wu .......................... | B05D 3/06 |
| 2010/0285561 A1 | 11/2010 | Suarez | |
| 2010/0316531 A1 | 12/2010 | Delattre | |
| 2012/0316086 A1 * | 12/2012 | Lin ....................... | G01N 27/447 506/26 |
| 2013/0116153 A1 | 5/2013 | Bowen et al. | |
| 2015/0044686 A1 | 2/2015 | Pallas | |

FOREIGN PATENT DOCUMENTS

| | | |
|---|---|---|
| CN | 103579531 | 2/2014 |
| CN | 104968427 | 10/2015 |
| EP | 1 364 702 A2 | 11/2003 |
| JP | 2003090815 A | 3/2003 |
| WO | WO 2007/007052 A2 | 1/2007 |
| WO | WO 2013/184796 A1 | 12/2013 |
| WO | WO 2014/133905 A1 | 9/2014 |
| WO | WO 2015/031849 A1 | 3/2015 |
| WO | WO 2015/095291 A1 | 6/2015 |

* cited by examiner

*Primary Examiner* — Peter L Vajda
*Assistant Examiner* — Nicholas E Brown
(74) *Attorney, Agent, or Firm* — Knobbe, Martens, Olson & Bear, LLP

(57) ABSTRACT

Embodiments provided herewith are directed to self-assembled methods of preparing a patterned surface for sequencing applications including, for example, a patterned flow cell or a patterned surface for digital fluidic devices. The methods utilize photolithography to create a patterned surface with a plurality of microscale or nanoscale contours, separated by hydrophobic interstitial regions, without the need of oxygen plasma treatment during the photolithography process. In addition, the methods avoid the use of any chemical or polishing steps after the deposition of a gel material to the contours.

21 Claims, 19 Drawing Sheets

CYTOP A+S coating
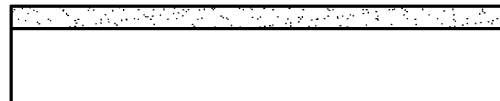
Shipley S1818/S1805 Photoresist coating
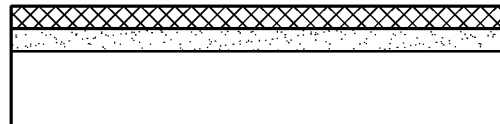
Patterning Stripping
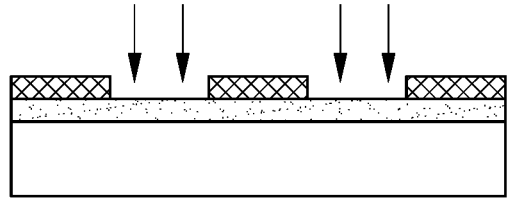
Deposition of silane coupling agent
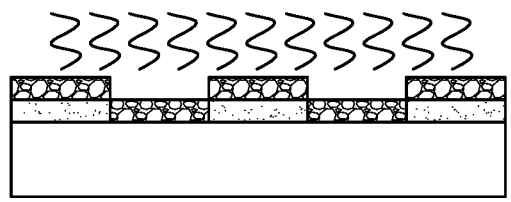
Spin coat hydrogel & cure
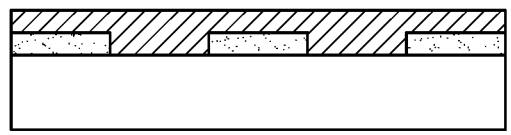
Rinse away excess hydrogel
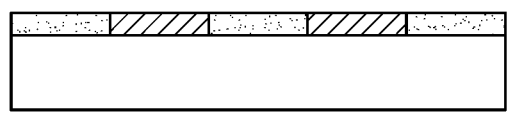
FIG. 5

CYTOP A+S coating
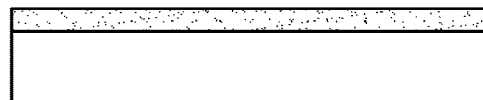
Fluorosurfactant coating (% Suflon-S651 in IPA)
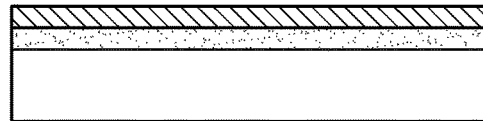
Photoresist coating
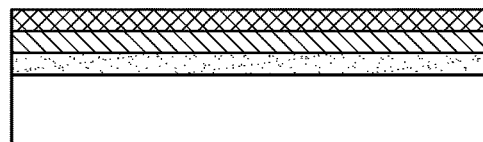
Patterning
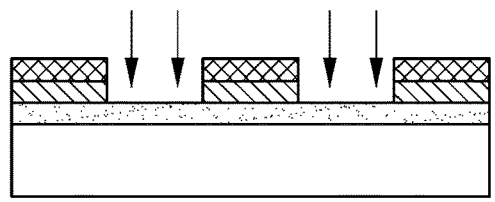
Deposition of Self assembled silane monolayer (Norbornene)
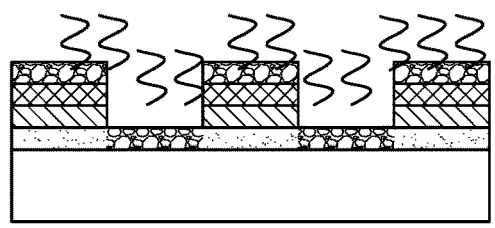
Spin coat hydrogel & cure
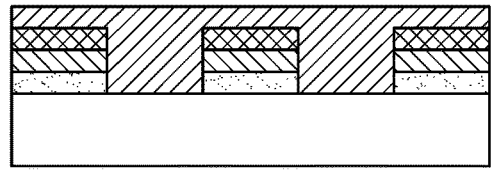
Resist lift-off / stripping
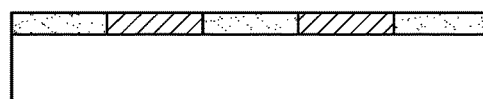
Rinse away excess hydrogel
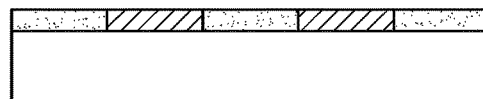
FIG. 8A

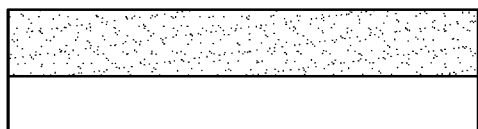 → Hydrophobic
O2 plasma
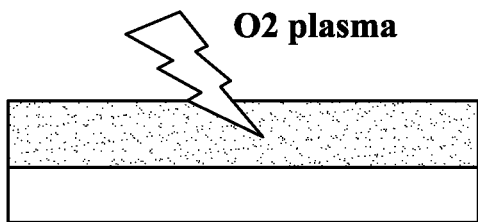 → Hydrophobic
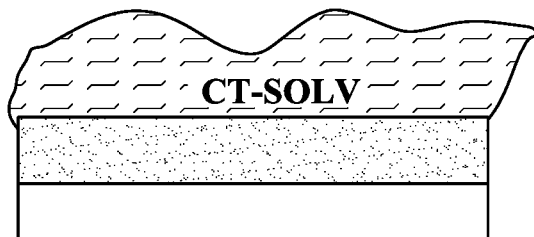 → Reflow in-solvent in LIQUID PHASE
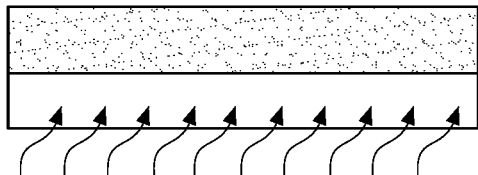 → Hydrophobic
Cure at low temp (50C)
FIG. 9A

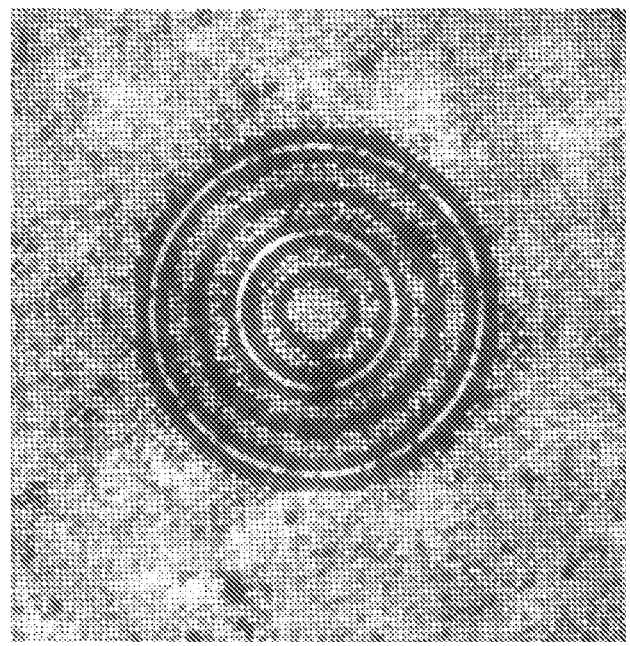
FIG. 12B 900nm wells
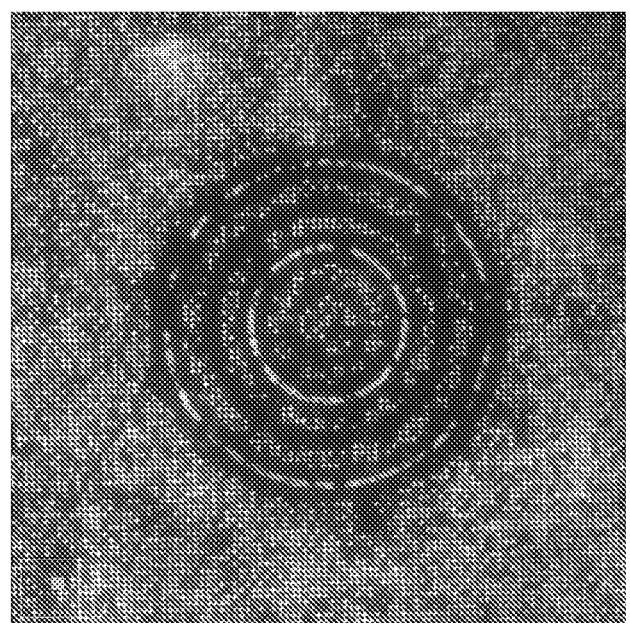
FIG. 12A 700nm wells

SELF ASSEMBLED PATTERNING USING PATTERNED HYDROPHOBIC SURFACES

INCORPORATION BY REFERENCE TO PRIORITY APPLICATIONS

The present application is a continuation of U.S. application Ser. No. 16/096,669, filed Oct. 25, 2018, to be issued as U.S. Pat. No. 10,900,076, which is a U.S. national phase application under § 371 of International Appl. No. PCT/US2017/033169, filed May 17, 2017, which claims the benefit of priority to U.S. Provisional Appl. No. 62/338,394, filed May 18, 2016, each of which is hereby incorporated by reference in its entirety.

BACKGROUND

In general, the present disclosure relates to the fields of photolithography patterning processes to produce micro- or nano-patterned surfaces for polynucleotide sequencing applications. More specifically, the present application relates to self-assembled methods of preparing patterned surfaces for flow cells or digital fluidic devices.

SUMMARY

Flow cells are devices that allow fluid flow through channels or wells within a substrate. Patterned flow cells that are useful in nucleic acid analysis methods include discrete wells having an active surface within inert interstitial regions. The surface of the flow cell is normally fabricated using the following steps: (1) wells are initially etched into a uniform substrate; (2) the wells and the interstitial regions are functionalized with a silane and a gel material; (3) excess gel material covering the interstitial regions is removed via a polishing process; and (4) the gel material in the wells is then grafted with single stranded primer DNA to provide a flow cell surface for the downstream sequencing applications. In this case, some of the gel material is wasted in the polishing step of the fabrication workflow. In addition, the surface energy of the interstitial regions largely depends on the starting substrate.

Embodiments relate to self-assembled methods of preparing a patterned surface for sequencing applications. The patterned surface may include, for example, a patterned flow cell or a patterned surface for a digital fluidic device. In some embodiments, the methods utilize photolithography to create a patterned surface with a plurality of microscale or nanoscale contours separated by hydrophobic interstitial regions while eliminating the need for oxygen plasma surface or other treatment before deposition of a photoresist. In addition, some embodiments avoid the use of chemical or mechanical polishing steps after the deposition of a gel material over the contours.

Some embodiments described herein are related to methods of preparing a patterned surface with gel-coated contours by: providing a solid support comprising a surface, the surface comprising a continuous hydrophobic coating layer; disposing a photoresist on the hydrophobic coating layer of the solid support to cover the hydrophobic coating layer; and patterning the photoresist layer by photolithography (or other suitable methods known in the art and/or described herein) to form micro-scale or nano-scale contours on the surface; and depositing a layer of a gel material within the micro-scale or nano-scale contours, wherein the gel material is capable of covalently bonding to oligonucleotides. In some embodiments, the micro-scale or nano-scale contours are formed by etching off portions of the hydrophobic coating layer. In some embodiments, the micro-scale or nano-scale contours are separated from each other by hydrophobic interstitial regions comprising the hydrophobic coating layer. In some embodiments, at least a portion of the micro-scale or nano-scale contours are free of hydrophobic coating. In some embodiments, the methods do not require a plasma surface modification treatment (e.g., descum or oxygen plasma treatment, corona treatment, heating, chemical or liquid activation, or other treatment used to increase surface energy and improve bonding characteristics) of the surface prior to disposing the photoresist. In certain embodiments, the contours are wells.

Some embodiments described herein are related to methods of preparing a patterned surface for analytic applications, the methods include: providing a solid support comprising a surface, the surface comprising a continuous hydrophobic coating layer; disposing a photoresist on the hydrophobic coating layer of the solid support to cover the hydrophobic coating layer; patterning the photoresist layer by photolithography (or other suitable methods) to form micro-scale or nano-scale contours on the surface separated by hydrophobic interstitial regions; removing the photoresist; and applying a layer of binding material, such as a silane layer, to the surface to cover at least a portion of the contours and a portion of the hydrophobic interstitial regions. In some embodiments, the methods further include covalently attaching a gel material to the layer of binding material, such as silane. In some embodiments, the methods further include covalently attaching an oligonucleotide to the gel material. In some embodiments, the methods further include non-covalently attaching a gel material to the layer of binding material, such as silane. In some embodiments, the methods comprise applying a layer of gel material to the binding material layer or layer of silane.

Some embodiments described herein are related to methods of preparing a patterned surface for analytic applications, the methods include: providing a solid support comprising a surface, the surface comprising a continuous hydrophobic coating layer; disposing a photoresist on the hydrophobic coating layer of the solid support to cover the hydrophobic coating layer; patterning the photoresist layer by photolithography (or other suitable methods) to form micro-scale or nano-scale contours on the surface separated by hydrophobic interstitial regions; applying a layer of silane to the surface to cover at least a portion of the contours and a portion of the hydrophobic interstitial regions; and covalently attaching a gel material to the binding material layer or layer of silane. In some embodiments, the methods further include removing the photoresist to expose the hydrophobic layer in hydrophobic interstitial regions.

In some embodiments, the binding material affixes, covalently or non-covalently, the gel material to the hydrophobic coating layer and/or the solid support. In some embodiments, the gel material is covalently bound to the binding material, e.g., silane.

Some embodiments described herein are related to methods of preparing an array of polynucleotides, the methods include providing a solid support comprising a patterned surface, the surface comprising microscale and/or nanoscale contours coated with a gel material that is capable of covalently bonding to oligonucleotides, the surface is prepared by any of the methods described herein; and covalently attaching a plurality of first oligonucleotides and a plurality of second oligonucleotides to the gel material.

BRIEF DESCRIPTION OF THE DRAWINGS

FIG. 5 illustrates one embodiment of an improved workflow for creating a patterned surface.

FIG. 8A illustrates one embodiment of an improved patterning workflow for creating a patterned surface using lift-off method.

FIG. 9A illustrates an example of a liquid phase reflow process.

FIGS. 12A and 12B show that DNA cluster size and intensity are tunable with different well sizes. FIG. 12A shows SYTOX®-dyed clusters grown in 0.7 micron diameter wells and 1.75 micron pitch with the surface layers as depicted in FIG. 11B. FIG. 12B shows SYTOX®-dyed clusters grown in 0.9 micron diameter wells and 1.75 micron pitch.

FIG. 13A is a first base image showing super-imposed C and T channels and circular fiducial indicating patterning of clusters within CYTOP nanowells, obtained using a polish-free patterning method. FIG. 13B shows the mismatch rate (error rate) for read 1 and read 2 of this run, each 150 cycles. The achieved error rate is similar to that expected from MiSeq runs (approx. 2% at the end of 150 cycles). This figure also demonstrates that paired-end turn-around is compatible with the polish-free patterning method. FIG. 13C shows the q-score (quality score) of the reads as a function of cycle for the run, while provides a measure of quality of the base output. CYTOP patterning is shown to be compatible with sequencing chemistry and is robust, slowing thousands of flow exchanges to finish 2×150 bps sequencing. Details for these experiments are described in Example 3.

DETAILED DESCRIPTION

Figure 1:
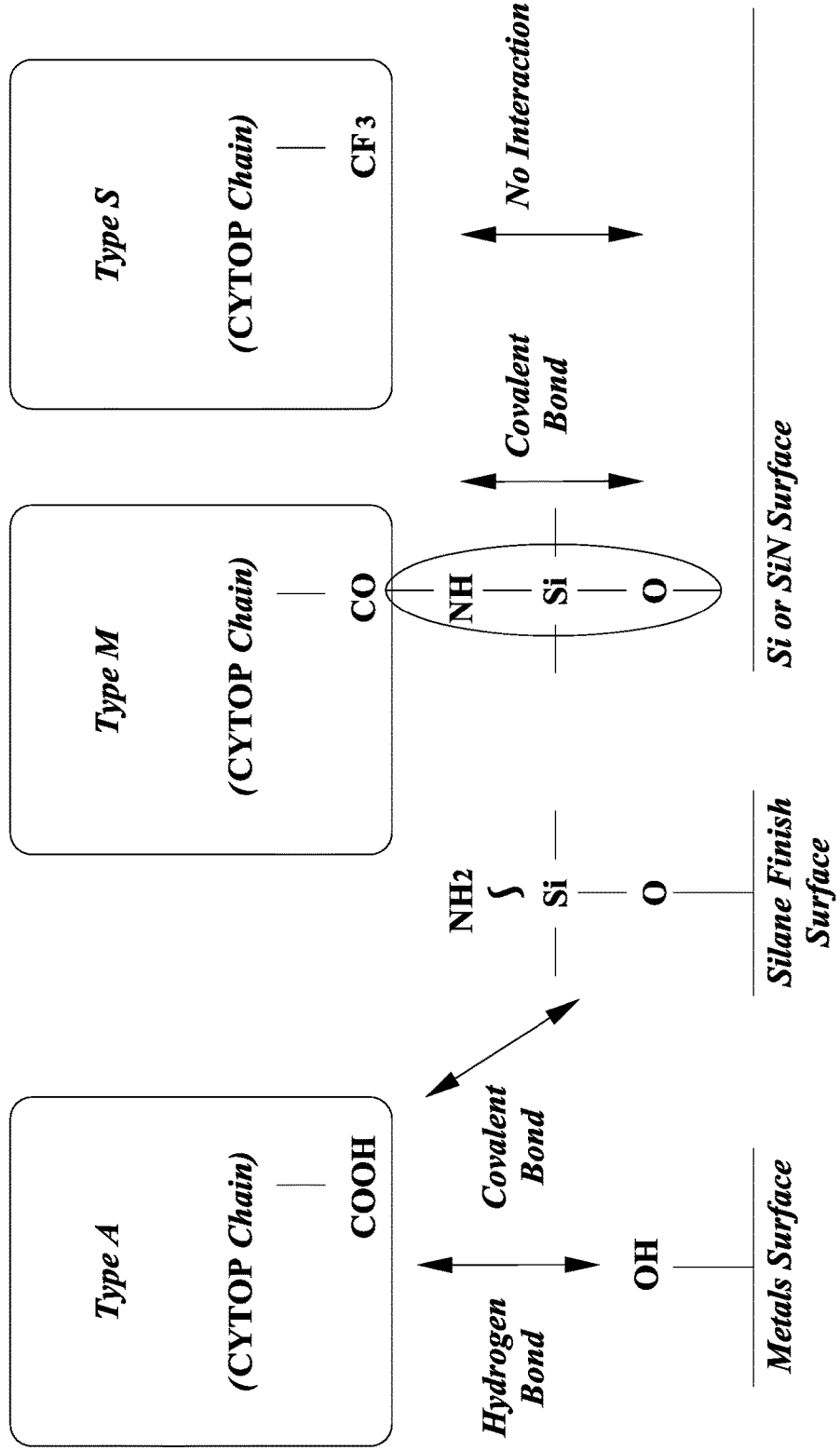
FIG. 1 is a schematic diagram showing three types of perfluorinated polymers (CYTOP-A, CYTOP-M and CYTOP-S) that may be used to create the hydrophobic interstitial regions on the patterned surface of a substrate.

Embodiments relate to methods of preparing a patterned surface that can be used in analysis and synthesis of analytes of interest such as biological components including, but not limited to, cells, subcellular components, and molecules. Exemplary biological molecules include, but are not limited to nucleic acids, oligonucleotides, nucleotides, amino acids, peptides, proteins, polysaccharides, sugars, metabolites, enzyme cofactors, and the like. Particularly useful analytical processes for which the patterned surfaces can be used include, for example, nucleic acid sequencing applications. In one embodiment, the patterned surface is part of a flow cell or electrowetting fluidic device. In some embodiments are used nanofabrication techniques, such as photoetching, photoengraving, or photolithography, or other patterning methods such as e-beam lithography, nano imprint lithography, nano-stamping, or direct ablation, to create the patterned surface with a plurality of microscale or nanoscale contours, separated by hydrophobic interstitial regions. Where photolithography is mentioned herein as a patterning technique, these other methods may also be used to pattern the surfaces. The patterned surface may be manufactured without the need of oxygen plasma treatment of the substrate surface prior to photolithography. A gel material can be deposited on the surface and differential hydrophobic/hydrophilic characteristics of the contours and interstitial regions on the surface can be exploited to conveniently remove gel material from some regions of the surface while retaining gel material at desired features. For example, gel material can be retained at silanated wells and removed from hydrophobic interstitial regions around the wells. Such embodiments can be particularly advantageous by avoiding the use of harsh chemical or mechanical polishing steps to remove gel material from interstitial regions after the deposition of the gel material over the surface. In some embodiments, the hydrophobic interstitial regions comprise a perfluorinated polymer such as CYTOP-S.

The section headings used herein are for organizational purposes only and are not to be construed as limiting the subject matter described.

Surface Preparations

Some embodiments described herein are related to methods of preparing a patterned surface that is configured to bind analytes, such as nucleic acid molecules, in predetermined positions, and are related to the patterned surfaces. For example, the patterned surface may have regions, or contours, that have differential hydrophobic and hydrophilic characteristics. This can allow surface chemistries to be differentially applied to the surface. For example, contours, wells, or other features formed on a surface can be treated to contain reactive silanes and/or a gel material that is absent from interstitial regions that separate the contours, wells, or other features from each other. In one embodiment, the contours or wells are coated with a gel or similar polymeric material that is capable of binding to, or is bound to, analytes such as nucleic acid molecules. In this embodiment, the patterned surface can be created by starting with a solid support comprising a surface having a continuous hydrophobic coating layer. A layer of photoresist can then be deposited onto the hydrophobic coating layer of the solid support to cover the hydrophobic coating layer. The photoresist layer can then be patterned by photolithography using a photomask comprising a plurality of micro-scale and/or nano-scale patterns such that the micro-scale or nano-scale patterns are transferred to the surface to form micro-scale or nano-scale contours on the hydrophobic coating layer. A layer of a gel material can then be deposited within the micro-scale or nano-scale contours, wherein the gel material is capable of covalently bonding to oligonucleotides.

During photolithography, photoresist is exposed to a pattern of light (for example, UV light) by using a patterned photomask. The exposure to light causes a chemical change that allows the portion of the photoresist that is exposed to be removed by a developer solution to expose patches of the underlying hydrophobic coating layer. After the photoresist is developed (for example, by following a standard recipe for the specific photoresist product used in the process), micro-scale or nano-scale contours are formed by etching off portions of the exposed hydrophobic coating layer on the surface. In some embodiments, the micro-scale or nano-scale contours are separated from each other by hydrophobic interstitial regions comprising the hydrophobic coating layer. In some embodiments, at least a portion of the micro-scale or nano-scale contours are free of hydrophobic coating. In some embodiments, the contours comprise depressions, such as channels or wells (for example, microwells or nanowells). In another embodiment, the contours comprise protrusions, such as ridges, posts, or cones (for example, nanoposts or nanocones).

In some embodiments of the methods described herein, the hydrophobic coating layer comprises a fluorinated polymer, a perfluorinated polymer, or a silicon polymer, or a mixture thereof. The polymer backbone may be carbon or silicon, or a combination thereof. In some embodiments, the fluorinated polymer is, for example, an amorphous fluoropolymer (optionally 2,3-linked perfluorinated THF monomers, optionally with pendant functional groups such as carboxyl, silylated amide, or trifluoromethyl termini, e.g., CYTOP-M, CYTOP-S, CYTOP-A, see FIG. 1), a polytetrafluoroethylene (such as Teflon), parylen (e.g., grades A, F, HT), a fluorinated hydrocarbon, a fluoroacrylic copolymer (such as Cytonix Fluoropel), a fluorosilane, or a plasma-deposited fluorocarbon. In some embodiments, the silicon polymer is polydimethylsiloxane or a siloxane. In some embodiments, the hydrophobic coating layer comprises a perfluorinated polymer. In some particular embodiments, the perfluorinated polymer is selected from CYTOP-M, CYTOP-S, or CYTOP-A. In one embodiment, the perfluorinated polymer comprises or is CYTOP-S. In another embodiment, the perfluorinated polymer comprises CYTOP-M. In another embodiments, the perfluorinated polymer is a mixture of CYTOP-S and CYTOP-A. In some embodiments, the hydrophobic coating layer is in direct contact with the surface. The direct contact may be via covalent or non-covalent bonding. In some other embodiments, the hydrophobic coating layer is in contact with the surface via a first adhesion promoting layer. In one example, the first adhesion promoting layer comprises a functionalized silane or adhesion promoter; an exemplary first adhesion layer comprises CYTOP-A, (3-aminopropyl)trimethoxysilane (APTMS), or (3-aminopropyl)triethyoxysilane (APTES), or combinations thereof.

To dispose the photoresist on the hydrophobic coating layer for photolithography often requires some degree of match in surface energy between the hydrophobic coating layer and the photoresist layer to be deposited above it. In some embodiments, the hydrophobic coating layer is prepared for photoresist application using an oxygen plasma treatment. In some instances, the oxygen plasma treatment (such as descum treatment) may damage the chemical structure of the hydrophobic coating layer. The present methods remove or reduce the need for the pre-treatment of the surface prior to disposing the photoresist by offering two alternative processes.

In one alternative, a photoresist may be used such that it is in direct contact with the hydrophobic coating layer without oxygen plasma pre-treatment. In some embodiments, the photoresist is a positive photoresist. In other embodiments, the photoresist is a negative photoresist. In some embodiments, the photoresist is selected from Shipley S1800™ series photoresists, for example, Shipley S1818 (MICROPOSIT™ S1818™) and Shipley S1805 (MICROPOSIT™ S1805™).

In another alternative, an adhesion promoting layer may be used to reduce the surface energy mismatch between the hydrophobic coating layer and the photoresist layer. In some embodiments, the adhesion promoting layer comprises a fluorinated surfactant. In some such embodiments, the fluorinated surfactant is selected from Surflon S-651, Novec FC-4430, Novec FC-4432, Novec FC-4434, Novec FC-5210, Zonyl FSN-100, Zonyl FS-300, Zonyl FS-500, Capstone FS-10, Capstone FS-30, Capstone FS-60, Capstone FS-61, Capstone FS-63, Capstone FS-64, or Capstone FS-65, or combinations thereof. In one embodiment, the fluorinated surfactant comprises Surflon S-651.

Direct Gel Patterning

Some embodiments described herein are related to methods of preparing a patterned surface for analytic applications by a direct gel patterning method. In the direct gel patterning method, a solid support having a surface is provided with a continuous hydrophobic coating layer. A photoresist is disposed onto the hydrophobic coating layer. The photoresist layer is then patterned by photolithography using a photomask comprising a plurality of micro-scale or nano-scale patterns such that the micro-scale or nano-scale patterns are transferred to the surface to form micro-scale or nano-scale contours on the surface separated by hydrophobic interstitial regions. In some embodiments, the micro-scale or nano-scale contours are formed by etching off portions of the hydrophobic coating layer and the micro-scale or nano-scale contours are separated from each other by hydrophobic interstitial regions comprising the hydrophobic coating layer. The photoresist is then removed and a layer of silane is applied to the surface to cover at least a portion of the contours and a portion of the hydrophobic interstitial regions. A gel is then added to the surface. Nucleic acids can be attached to the gel before, after, or during to the attachment of the gel to the surface. These methods are also known as direct patterning methods.

In the direct patterning methods described herein, the remaining photoresist that is not exposed to light need not undergo any chemical change and can remain on the hydrophobic interstitial regions after the developing process. The remaining photoresist may be removed by various reagents, depending on the type of photoresist used. For example, photoresist lift-off resist (LOR) may be removed by MICROCHEM Remover PG. In some embodiments, the remaining photoresist is removed by acetone, for example, by sonication in acetone solution. The second adhesion promoting layer may be removed with the photoresist at the same time. Alternatively, the second adhesion promoting layer is removed subsequent to the photoresist using a different removal reagent. After the removal of the remaining photoresist that covers the hydrophobic interstitial regions, the hydrophobic coating layer that is exposed can be subjected to subsequent silane deposition.

In some embodiments, a gel material is covalently attached to the layer of silane. In some embodiments, the methods further include curing the gel material. The curing process may be done at various conditions, depending on the type of gel material used, as understood by one of ordinary skill in the art. In some embodiments, the curing is done by incubating the gel material deposited on the silane layer in an oven. In some further embodiments, the methods further include removing excess gel material such that the hydrophobic interstitial regions are substantially free of the gel material. In some embodiments, the removal of the gel material can be simply done by rinsing in water.

In some embodiments, the methods described herein also eliminate the need for chemical or mechanical polishing after the deposition of the gel material.

In some embodiments, the methods further include covalently attaching a nucleic acid (e.g., oligonucleotide) to the gel material.

Lift-Off Gel Patterning

Some further embodiments described herein are related to methods of preparing a patterned surface by a Lift-Off gel patterning method. This method can include using solid support having a continuous hydrophobic coating layer and disposing a photoresist layer on the hydrophobic coating layer. The photoresist can then be patterned by photolithography using a photomask comprising a plurality of microscale or nano-scale patterns such that the micro-scale or nano-scale patterns are transferred to the surface to form micro-scale or nano-scale contours on the surface separated by hydrophobic interstitial regions. In some embodiments, the micro-scale or nano-scale contours are formed by etching off portions of the hydrophobic coating layer. A layer of silane can then be applied to the surface to cover at least a portion of the contours and a portion of the hydrophobic interstitial regions and a gel material can be covalently attached to the layer of silane. These methods are also known as lift-off methods.

In the lift-off methods described, rather than removing the photoresist right after pattern transfer as described in the direct patterning process, the methods can directly apply a layer of silane to the surface to cover at least a portion of the contours and a portion of the hydrophobic interstitial regions in the presence of the photoresist. Then, a gel material may be covalently attached to the layer of silane. In some embodiments, the methods further include curing the gel material. The curing process may be done at various conditions, depending on the type of gel material used, as understood by one of ordinary skill in the art. In some embodiments, the curing is done by incubating the gel material deposited on the silane layer in an oven.

After the gel material is immobilized on the silane layer, the remaining photoresist in the interstitial regions can then be removed or "lifted off" thereby exposing the underlying hydrophobic coating layer. The remaining photoresist may be removed by various reagents, depending on the type of photoresist used. For example, photoresist LOR may be removed by MICROCHEM Remover PG. In some embodiments, the remaining photoresist is removed by acetone, for example, sonication in acetone solution. The second adhesion promoting layer may be removed with the photoresist at the same time. Alternatively, the second adhesion promoting layer is removed subsequent to the photoresist using a different removal reagent. In one embodiment, the photoresist and the second adhesion promoting layer are both removed by acetone.

In some embodiments, the methods further include removing excess gel material that is not immobilized to the silane layer.

In some embodiments, the methods further include covalently attaching a nucleic acid (e.g. an oligonucleotide) to the gel material.

In methods or compositions set forth herein (e.g., surface preparation, direct patterning, and lift-off methods), the silane used herein may comprise functional groups to forming covalent bonding with the gel materials. Non-limiting examples of the functional groups in the silane include vinyl, acryloyl, alkenyl, cycloalkenyl, heterocycloalkenyl, alkynyl, cycloalkynyl, heterocycloalkynyl, nitrene, aldehyde, hydrazinyl, glycidyl ether, epoxy, carbene, isocyanate or maleimide, or optionally substituted variants or combinations thereof. For example, the silane used herein may comprise an amino group (such as APTES or APTMS). In some preferred embodiment, the silane used herein comprises norbornene derivatized silane. In one embodiment, the silane comprises [(5-bicyclo[2.2.1]hept-2-enyl)ethyl]trimethoxysilane. The silane may be deposited on the surface of the solid support via chemical vapor deposition.

In methods or compositions set forth herein (e.g., surface preparation, direct patterning, and lift-off methods), the gel material that may be used includes, but is not limited to hydrogels or polymers. Useful hydrogels include, but are not limited to, silane-free acrylamide (SFA) polymer, poly(N-(5-azidoacetamidylpentyl)acrylamide-co-acrylamide) (PAZAM), polyacrylamide polymers formed from acrylamide and an acrylic acid or an acrylic acid containing a vinyl group as described, for example, in WO 00/31148 (incorporated herein by reference); polyacrylamide polymers formed from monomers that form [2+2] photo-cycloaddition reactions, for example, as described in WO 01/01143 or WO 03/014392 (each of which is incorporated herein by reference); or polyacrylamide copolymers described in U.S. Pat. No. 6,465,178, WO 01/62982 or WO 00/53812 (each of which is incorporated herein by reference). Chemically-treated variants of these gel materials are also useful, such as a hydrogel having reactive sites that is capable of reacting with oligonucleotides having corresponding reactive groups (for example, PAZAM is capable of reacting with a 5'- or 3'-alkynyl modified oligonucleotides). Other useful gels are those that are formed by a temperature dependent change in state from liquid to gelatinous. Examples include, but are not limited to agar, agarose, or gelatin. In some embodiments, the gel material is covalently attached to the silane layer.

In some embodiments, a gel material that is used will include reactive sites. The term "reactive site" as used herein means a site on the gel described herein that can be used to attach one or more molecules to the gel material, and/or to attach the gel material to the surface, by way of a chemical reaction or molecular interaction. Non-limiting examples of reactive sites include azido, optionally substituted amino, Boc-protected amino, hydroxy, thiol, alkynyl, alkenyl, halo, epoxy, tetrazinyl, or aldehyde. In some embodiments, the gel material comprises a polymer with azido functional groups as reactive sites. In particular embodiments, the gel material comprises PAZAM. PAZAM is capable of reacting with norbornene-derivatized silane to form covalent bonding via catalyst free strain-promoted cycloaddition. In some embodiments, the reactive sites of the gel material are also capable of forming covalent bonding with functionalized oligo nucleotides for the purpose of primer grafting. In some alternative embodiments, the gel material is pre-grafted with primers before reacting with the silane layer.

In some other embodiments, a gel-forming (e.g., polymerizable) material may be provided on the surface in a liquid state and subsequently converted to a gel. Examples of polymerizable materials include, without limitation, acrylamide, methacrylamide, hydroxyethyl methacrylate, N-vinyl pyrolidinone, or derivatives thereof. Such materials are useful for preparing hydrogels. In some embodiments, the polymerizable material can include two or more different species of compound that form a co-polymer. For example, two or more different species of acrylamide, methacrylamide, hydroxyethyl methacrylate, N-vinyl pyrolidinone, or derivatives thereof can function as co-monomers that polymerize to form a copolymer hydrogel.

Patterned Surfaces and Solid Supports

Described herein is a patterned surface with gel-coated contours comprising a solid support comprising:
  a surface, the surface comprising a continuous hydrophobic coating layer;
  a photoresist layer on the hydrophobic coating layer of the solid support, wherein the photoresist layer comprises micro-scale or nano-scale contours; and
  a layer of gel material within the micro-scale or nano-scale contours, wherein the gel material is capable of covalently bonding to oligonucleotides.

In some embodiments, the contours are separated by hydrophobic interstitial regions, and further comprise a layer of binding material (such as a layer of silane) covering at least a portion of the contours and a portion of the hydrophobic interstitial regions. In some embodiments, at least a portion of the micro-scale or nano-scale contours are free of the hydrophobic coating. In some embodiments, the contours comprise wells. In some embodiments, the surface comprises a hydrophobic coating layer, a photoresist layer on the hydrophobic coating layer of the solid support, wherein the photoresist layer comprises micro-scale or nano-scale contours; a layer of binding material or silane covering at least a portion of the contours and at least a portion of the hydrophobic interstitial regions.

In some embodiments, the hydrophobic coating layer comprises a fluorinated polymer, a perfluorinated polymer, or a silicon polymer, or a mixture thereof. In some embodiments, the hydrophobic coating layer comprises an amorphous fluoropolymer, CYTOP-M, CYTOP-S, CYTOP-A, a polytetrafluoroethylene, Teflon, parylen, a fluorinated hydrocarbon, a fluoroacrylic copolymer, Cytonix Fluoropel, a fluorosilane, a plasma-deposited fluorocarbon, a silicon polymer, a polydimethylsiloxane, or a siloxane, or a mixture thereof. In other embodiments, the hydrophobic coating layer comprises a perfluorinated polymer. In other embodiments, the hydrophobic coating layer comprises CYTOP-M, CYTOP-S, or CYTOP-A, or a mixture thereof. In other embodiments, the hydrophobic coating layer comprises CYTOP-S. In other embodiments, the hydrophobic coating layer comprises CYTOP-M. In other embodiments, the hydrophobic coating layer comprises CYTOP-S and CYTOP-A.

In some embodiments, the hydrophobic coating layer is in direct contact with the surface. In other embodiments, the hydrophobic coating layer is in contact with the surface via a first adhesion promoting layer. In some embodiments, the first adhesion promoting layer comprises CYTOP-A, APTMS, or APTES, or a combination thereof.

In some embodiments, the photoresist is in direct contact with the hydrophobic coating layer of the solid support. In other embodiments, the photoresist is in contact with the hydrophobic coating layer of the solid support via a second adhesion promoting layer. In some embodiments, the second adhesion promoting layer comprises a fluorinated surfactant. In some embodiments, the fluorinated surfactant is Surflon S-651, Novec FC-4430, Novec FC-4432, Novec FC-4434, Novec FC-5210, Zonyl FSN-100, Zonyl FS-300, Zonyl FS-500, Capstone FS-10, Capstone FS-30, Capstone FS-60, Capstone FS-61, Capstone FS-63, Capstone FS-64, or Capstone FS-65, or a combination thereof.

In some embodiments, the photoresist is a Shipley S1800™ series photoresist. In some embodiments, the photoresist is selected from Shipley S1818 (MICROPOSIT™ S1818™) and Shipley S1805 (MICROPOSIT™ S1805™).

In some embodiments, the gel material comprises PAZAM. In some embodiments, the gel material comprises PAZAM attached to nucleic acids.

In some embodiments, the surface further comprises (a) a binding material layer or (b) a silane layer, wherein the binding material layer or silane layer optionally comprises a norbornene derivatized silane, and wherein the binding material layer or silane layer covers at least a portion of the contours and a portion of the hydrophobic interstitial regions.

Also described herein are methods of preparing such patterned surfaces.

Definitions

Unless defined otherwise, all technical and scientific terms used herein have the same meaning as is commonly understood by one of ordinary skill in the art. The use of the term "including" as well as other forms, such as "include," "includes," and "included," is not limiting. The use of the term "having" as well as other forms, such as "have," "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

As used herein, common abbreviations are defined as follows:
  APTS Aminopropyl silane
  APTES (3-Aminopropyl)triethoxysilane
  APTMS (3-Aminopropyl)trimethoxysilane
  aq. Aqueous
  Azapa N-(5-azidoacetamidylpentyl) acrylamide
  ° C. Temperature in degrees Centigrade
  CA Contact angle
  CVD Chemical vapor deposition
  dATP Deoxyadenosine triphosphate
  dCTP Deoxycytidine triphosphate
  dGTP Deoxyguanosine triphosphate
  dTTP Deoxythymidine triphosphate
  g Gram(s)

h or hr Hour(s)
IPA Isopropyl Alcohol
m or min Minute(s)
mL Milliliter(s)
PAZAM Poly(N-(5-azidoacetamidylpentyl) acrylamide-co-acrylamide) of any acrylamide to Azapa ratio
rt Room temperature
SFA Silane Free Acrylamide as defined in U.S. Pat. Pub. No. 2011/0059865
SBS Sequencing-by-synthesis
SHP Semi-hydrophobic
ssDNA Single stranded DNA As used herein, the term "attached" refers to the state of two things being joined, fastened, adhered, connected or bound to each other. For example, an analyte, such as a nucleic acid, can be attached to a material, such as a gel or solid support, by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions.

As used herein, the term "array" refers to a population of different probes (e.g., probe molecules) that are attached to one or more substrates such that the different probes can be differentiated from each other according to relative location. An array can include different probes that are each located at a different addressable location on a substrate. Alternatively or additionally, an array can include separate substrates each bearing a different probe, wherein the different probes can be identified according to the locations of the substrates on a surface to which the substrates are attached or according to the locations of the substrates in a liquid. Exemplary arrays in which separate substrates are located on a surface include, without limitation, those including beads in wells as described, for example, in U.S. Pat. No. 6,355,431 B1, US 2002/0102578 and PCT Publication No. WO 00/63437. Exemplary formats that can be used in the invention to distinguish beads in a liquid array, for example, using a microfluidic device, such as a fluorescent activated cell sorter (FACS), are described, for example, in U.S. Pat. No. 6,524,793. Further examples of arrays that can be used in the invention include, without limitation, those described in U.S. Pat. Nos. 5,429,807; 5,436,327; 5,561,071; 5,583,211; 5,658,734; 5,837,858; 5,874,219; 5,919,523; 6,136,269; 6,287,768; 6,287,776; 6,288,220; 6,297,006; 6,291,193; 6,346,413; 6,416,949; 6,482,591; 6,514,751 and 6,610,482; WO 93/17126; WO 95/11995; WO 95/35505; EP 742 287; and EP 799 897.

As used herein, the term "covalently attached" or "covalently bonded" refers to the forming of a chemical bonding that is characterized by the sharing of pairs of electrons between atoms. For example, a covalently attached hydrogel refers to a hydrogel that forms chemical bonds with a functionalized surface of a substrate, as compared to attachment to the surface via other means, for example, adhesion or electrostatic interaction. It will be appreciated that polymers that are attached covalently to a surface can also be bonded via means in addition to covalent attachment.

As used herein, the term "coat," when used as a verb, is intended to mean providing a layer or covering on a surface. At least a portion of the surface can be provided with a layer or cover. In some cases the entire surface can be provided with a layer or cover. In alternative cases only a portion of the surface will be provided with a layer or covering. The term "coat," when used to describe the relationship between a surface and a material, is intended to mean that the material is present as a layer or cover on the surface. The material can seal the surface, for example, preventing contact of liquid or gas with the surface. However, the material need not form a seal. For example, the material can be porous to liquid, gas, or one or more components carried in a liquid or gas. Exemplary materials that can coat a surface include, but are not limited to, a gel, polymer, organic polymer, liquid, metal, a second surface, plastic, silica, or gas.

As used herein the term "analyte" is intended to include any of a variety of analytes that are to be detected, characterized, modified, synthesized, or the like. Exemplary analytes include, but are not limited to, nucleic acids (e.g., DNA, RNA or analogs thereof), proteins, polysaccharides, cells, nuclei, cellular organelles, antibodies, epitopes, receptors, ligands, enzymes (e g kinases, phosphatases or polymerases), peptides, small molecule drug candidates, or the like. An array can include multiple different species from a library of analytes. For example, the species can be different antibodies from an antibody library, nucleic acids having different sequences from a library of nucleic acids, proteins having different structure and/or function from a library of proteins, drug candidates from a combinatorial library of small molecules, etc.

As used herein the term "contour" is intended to mean a localized variation in the shape of a surface. Exemplary contours include, but are not limited to, wells, pits, channels, posts, pillars, and ridges. Contours can occur as any of a variety of depressions in a surface or projections from a surface. All or part of a contour can serve as a feature in an array. For example, a part of a contour that occurs in a particular plane of a solid support can serve as a feature in that particular plane. In some embodiments, contours are provided in a regular or repeating pattern on a surface.

Where a material is "within" a contour, it is located in the space of the contour. For example, for a well, the material is inside the well, and for a pillar or post, the material covers the contour that extends above the plane of the surface.

In some embodiments, where a second layer is said to "cover" a first layer, the second layer is in the form of a thin film on top of the first layer.

As used herein, the term "different", when used in reference to nucleic acids, means that the nucleic acids have nucleotide sequences that are not the same as each other. Two or more nucleic acids can have nucleotide sequences that are different along their entire length. Alternatively, two or more nucleic acids can have nucleotide sequences that are different along a substantial portion of their length. For example, two or more nucleic acids can have target nucleotide sequence portions that are different for the two or more molecules while also having a universal sequence portion that is the same on the two or more molecules. The term can be similarly applied to proteins which are distinguishable as different from each other based on amino acid sequence differences.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "feature" means a location in an array that is configured to attach a particular analyte. For example, a feature can be all or part of a contour on a surface. A feature can contain only a single analyte or it can contain a population of several analytes, optionally the several analytes can be the same species. In some embodiments, features are present on a solid support prior to attaching an analyte. In other embodiments the feature is created by attachment of an analyte to the solid support.

As used herein, the term "flow cell" is intended to mean a vessel having a chamber where a reaction can be carried out, an inlet for delivering reagents to the chamber and an outlet for removing reagents from the chamber. In some embodiments, the chamber is configured for detection of the reaction that occurs in the chamber (e.g. on a surface that is in fluid contact with the chamber). For example, the chamber can include one or more transparent surfaces allowing optical detection of arrays, optically labeled molecules, or the like in the chamber. Exemplary flow cells include, but are not limited to those used in a nucleic acid sequencing apparatus such as flow cells for the Genome Analyzer®, MiSeq®, NextSeq® or HiSeq® platforms commercialized by Illumina, Inc. (San Diego, Calif.); or for the SOLiD™ or Ion Torrent™ sequencing platform commercialized by Life Technologies (Carlsbad, Calif.). Exemplary flow cells and methods for their manufacture and use are also described, for example, in WO 2014/142841 A1; U.S. Pat. App. Pub. No. 2010/0111768 A1 and U.S. Pat. No. 8,951,781, each of which is incorporated herein by reference.

As used herein, the term "gel material" is intended to mean a semi-rigid material that is permeable to liquids and gases. Typically, a gel material can swell when liquid is taken up and can contract when liquid is removed, e.g., by drying. Exemplary gels include, but are not limited to, those having a colloidal structure, such as agarose; polymer mesh structure, such as gelatin; or cross-linked polymer structure, such as polyacrylamide, silane free acrylamide (see, for example, US Pat. App. Pub. No. 2011/0059865 A1), PAZAM (see, for example, U.S. Pat. No. 9,012,022, which is incorporated herein by reference), and polymers described in U.S. Patent Pub. No. 2015/0005447, and U.S. application Ser. No. 14/927,252, all of which are incorporated by reference in their entireties. Particularly useful gel material will conform to the shape of a well or other contours where it resides. Some useful gel materials can both (a) conform to the shape of the well or other contours where it resides and (b) have a volume that does not substantially exceed the volume of the well or contours where it resides. In some particular embodiments, the gel material is a polymeric hydrogel.

As used herein, the term "interstitial region" refers to an area in a substrate or on a surface that separates other areas of the substrate or surface. For example, an interstitial region can separate one contour or feature from another contour or feature on the surface. The two regions that are separated from each other can be discrete, lacking contact with each other. In many embodiments the interstitial region is continuous whereas the contours or features are discrete, for example, as is the case for an array of wells in an otherwise continuous surface. The separation provided by an interstitial region can be partial or full separation. Interstitial regions will typically have a surface material that differs from the surface material of the contours or features on the surface. For example, contours of an array can have an amount or concentration of gel material or analytes that exceeds the amount or concentration present at the interstitial regions. In some embodiments the gel material or analytes may not be present at the interstitial regions.

As used herein, the terms "nucleic acid" and "nucleotide" are intended to be consistent with their use in the art and to include naturally occurring species or functional analogs thereof. Particularly useful functional analogs of nucleic acids are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g., found in ribonucleic acid (RNA)). A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid or nucleotide are known in the art. The terms "probe" or "target," when used in reference to a nucleic acid, are intended as semantic identifiers for the nucleic acid in the context of a method or composition set forth herein and does not necessarily limit the structure or function of the nucleic acid beyond what is otherwise explicitly indicated. The terms "probe" and "target" can be similarly applied to other analytes such as proteins, small molecules, cells, or the like.

As used herein, the term "fluorinated" refers to a molecule containing at least one fluorine atom. As used herein, the term "perfluorinated" refers to a molecule containing two or more fluorine atoms. In some embodiments, perfluorinated molecules are hydrocarbon-containing molecules in which the hydrogen atoms on sp3-hybridized carbons are replaced with fluorine atoms. For example, certain perfluorinated polymers described herein contain a perfluoroalkyl group or a perfluoroalkylene moiety.

As used herein, the term "photoresist" and derivatives thereof refers to a light-sensitive material used in processes such as photolithography, photoetching, or photoengraving to form a patterned coating on a surface. Photoresist materials change solubility with respect to a developer solution when exposed to certain wavelengths of light. Photoresist layers may be composed of positive (exposed region becomes soluble) or negative (exposed region becomes insoluble) photoresist material.

As used herein, the term "pitch," when used in reference to contours or features on a surface, is intended to refer to the center-to-center spacing for adjacent features. A pattern of features can be characterized in terms of average pitch. The pattern can be ordered such that the coefficient of variation around the average pitch is small or the pattern can be random in which case the coefficient of variation can be relatively large. In either case, the average pitch can be, for example, at least about 10 nm, 0.1 µm, 0.2 µm, 0.3 µm, 0.4 µm, 0.5 µm, 1 µm, 5 µm, 10 µm, 100 µm or more, or a range defined by any of the two preceding values (e.g., 10 to 100 nm, 10 to 200 nm, 200 to 400 nm, 300 to 500 nm). Alternatively or additionally, the average pitch can be, for example, at most about 100 µm, 10 µm, 5 µm, 1 µm, 0.5 µm, 0.1 µm or less, or a range defined by any of the two preceding values. Of course, the average pitch for a particular pattern of features can be between one of the lower values and one of the upper values selected from the ranges above.

As used herein, the term "repeating pattern," when used in reference to features, is intended to mean that the relative locations of a subset of features or contours in one region of the object is the same as the relative locations of a subset of features or contours in at least one other region of the object.

Generally, the repeat occurs in the x and y dimensions. The one region is typically adjacent to that other region in the pattern. The relative locations for features in one region of a repeating pattern are generally predictable from the relative locations of contours in another region of the repeating pattern. The subset used for the measure will generally include at least 2 features but can include at least, 3, 4, 5, 6, 10 or more features. Alternatively or additionally, the subset used for the measure can include no more than 2, 3, 4, 5, 6, or 10 features. Exemplary repeating patterns include square lattices, rectangular lattices, rhombic lattices, hexagonal lattices and oblique lattices. A repeating pattern can include multiple repetitions of a sub-pattern.

As used herein, the term "segregate," when used in reference to a gel material on two contours (or at two separate features), means to separate or isolate the gel material on one of the contours (or at one of the features) from the gel material on the other contour (or at the other feature). Thus, the gel material on the first contour (or at the first feature) is not in direct contact with the gel material in the other well (or at the other feature). In some embodiments, the term "segregate" is used in reference to a gel material in two wells, and means to separate or isolate the gel material in one of the well from the gel material in the other well. In some embodiments, the gel material in the two wells (or at the two features) is in indirect contact, for example, via a solution that contacts the two wells (or features). Alternatively, the gel material in the two wells (or at the two features) is not even in indirect contact. An interstitial region on a surface can segregate the gel material in two wells (or at two features) by being devoid of the gel material. In particular embodiments, a gel material can be discontinuous on a surface, being present at features, such as wells, but not present at interstitial regions between the features.

As used herein, the term "surface" is intended to mean an external part or external layer of a solid support or gel material. The surface can be in contact with another material such as a gas, liquid, gel, polymer, organic polymer, second surface of a similar or different material, metal, or coat. The surface, or regions thereof, can be substantially flat or planar. The surface can have surface contours such as wells, pits, channels, ridges, raised regions, pegs, posts or the like.

As used herein, the term "solid support" refers to a rigid substrate that is insoluble in aqueous liquid. The substrate can be non-porous or porous. The substrate can optionally be capable of taking up a liquid (e.g., due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (e.g., acrylics, polystyrene and copolymers of styrene and other materials, polypropylene, polyethylene, polybutylene, polyurethanes, Teflon™, cyclic olefins, polyimides, etc.), nylon, ceramics, resins, Zeonor, silica or silica-based materials including silicon and modified silicon, carbon, metals, inorganic glasses, optical fiber bundles, and polymers. Particularly useful solid supports for some embodiments are components of a flow cell or located within a flow cell apparatus.

As used herein, the term "well" refers to a discrete contour in a solid support having a surface opening that is completely surrounded by interstitial region(s) of the surface. Wells can have any of a variety of shapes at their opening in a surface including but not limited to round, elliptical, square, polygonal, star shaped (with any number of vertices), etc. The cross section of a well taken orthogonally with the surface can be curved, square, polygonal, hyperbolic, conical, angular, etc. In some embodiments, the well is a microwell or a nanowell.

The embodiments set forth herein and recited in the claims can be understood in view of the above definitions.

FIG. 1 shows three types of fluoropolymers that may be used to create the hydrophobic interstitial regions of the patterned surface of a substrate. CYTOP-A, CYTOP-M, and CYTOP-S are commercially available amorphous perfluorinated polymers, each having the following backbone structure:

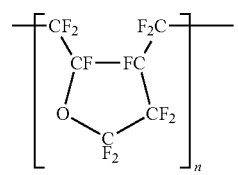

and different functional groups at both ends of the polymer chain. CYTOP-A has —C(O)OH end functional group. CYTOP-M has —C(O)NH—Si(OR)$_n$ functional group. CYTOP-S has —CF$_3$ functional groups. FIG. 1 also shows the type of possible interactions between each type of CYTOP polymer and the surface. It indicates that CYTOP-S has no chemical interaction with metal surface, silane finished surface, or Si/SiN surface due to the inertness of the —CF$_3$ functional group.

Figure 2A:
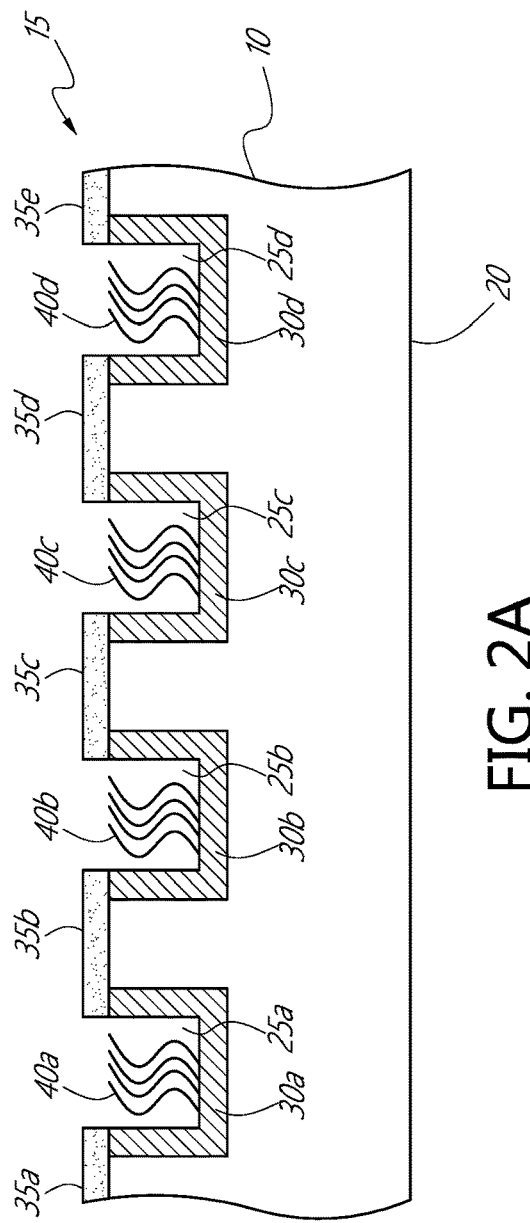
FIG. 2A is a cross section partial view of a patterned surface of a glass substrate including a plurality of wells and hydrophobic interstitial regions.

FIG. 2A is a diagrammatic cross section partial view of a patterned surface of a glass substrate 10. As shown, the glass substrate 10 has a top surface 15 and bottom surface 20. The top surface 15 has a plurality of wells 25a-25d formed in the top surface 15. Each of the wells 25a-25d has a polymer material or gel 30a-30d lining the interior walls of the wells. A series of hydrophobic interstitial regions 35a-35e are shown on the top surface 15 located between each of the wells 25a-25d. As shown, the polymer material or gel 30a-30d is deposited on the bottom of the wells 25a-25d and DNA clusters 40a-40d are covalently attached to the gel material 30a-30d.

Figure 2B:
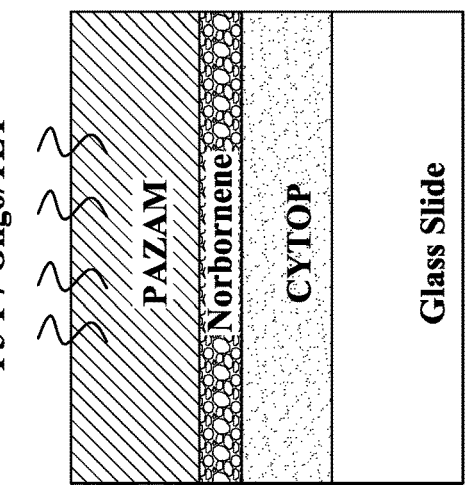
FIG. 2B is a magnified view of FIG. 2A showing three layers of materials on top of a glass slide.

FIG. 2B is a more detailed diagrammatic example of the surfaces described herein. As illustrated, the surface includes three layers of materials on top of the glass slide. The bottom CYTOP layer is in direct contact with the bottom glass surface. Deposited on top of the CYTOP material is a norbornene derivatized silane layer. On top of the norbornene layer is a top layer comprising PAZAM. A set of grafted P5/P7 oligonucleotide primers with the fluorophore TET™ attached are bound to the PAZAM layer of material. Sequences of P5 and P7 primers are set forth in U.S. Pat. No. 8,969,258, which is incorporated herein by reference.

Figure 2C:
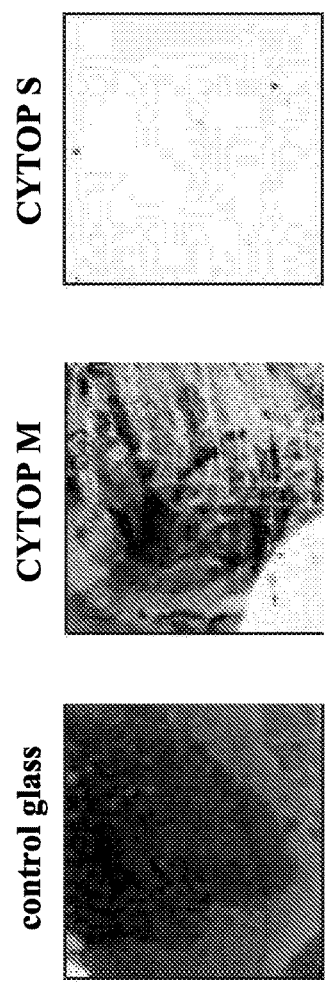
FIG. 2C are fluorescence images of three grafted glass surfaces from a Typhoon instrument.

FIG. 2C are fluorescence images of three grafted glass surfaces. A chemical inertness test was conducted on CYTOP-S and CYTOP-M. The left surface was used as a control and was not coated with any CYTOP polymers. The middle surface was coated with CYTOP-M and the right surface was coated with CYTOP-S. Then, each surface was treated with a norbornene derivatized silane, followed by PAZAM coupling and grafting of P5 and P7 oligonucleotides to the PAZAM. The presence or absence of PAZAM attached oligonucleotides was evaluated by hybridization of fluorescently labelled TET oligonucleotides (complementary to P5 and P7) and detection on a Typhoon fluorescence imager. The lack of TET oligo intensity on CYTOP-S treated surface indicates that oligonucleotide-grafted PAZAM was not immobilized on the CYTOP-S treated surface.

Figure 3:
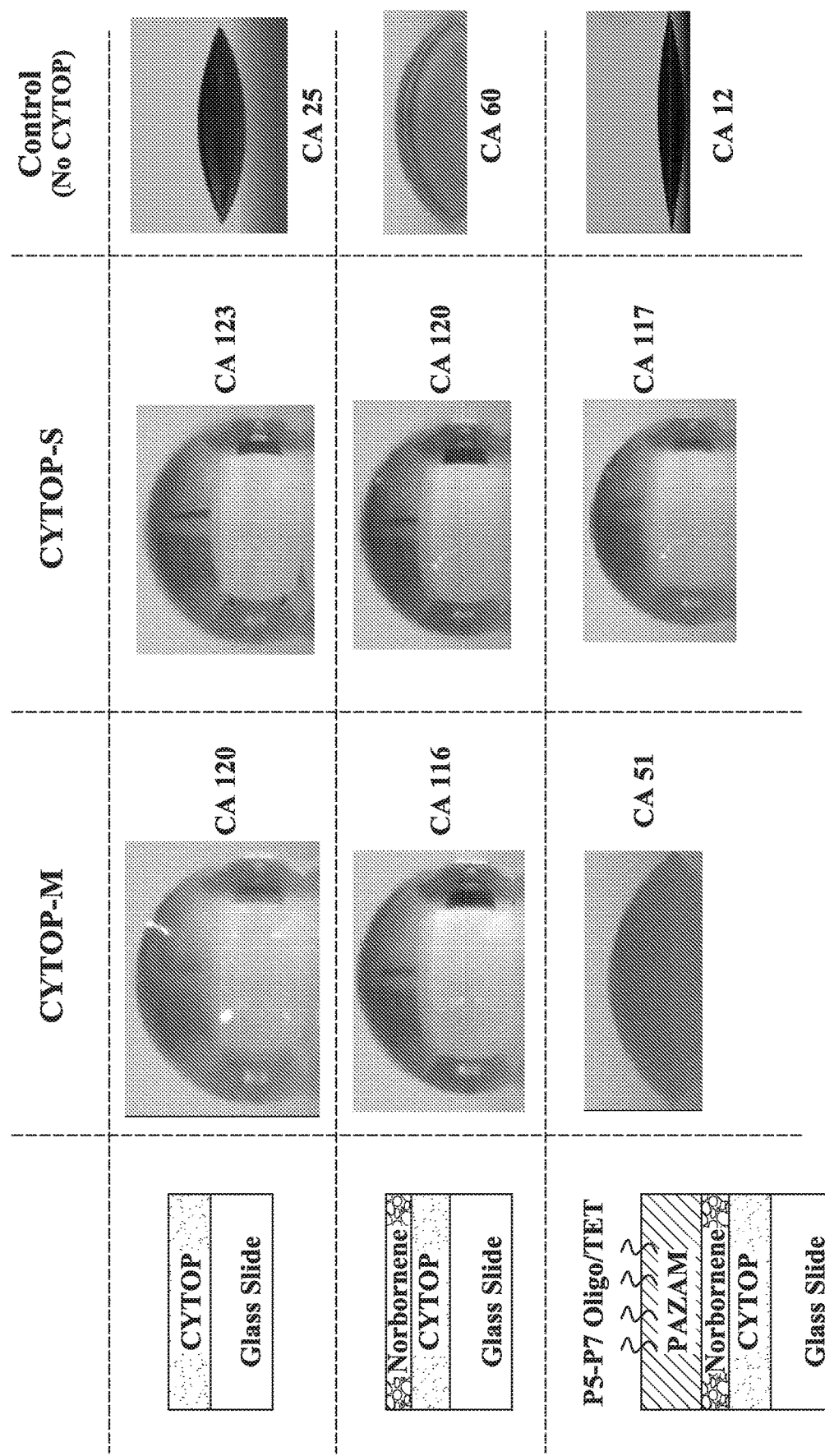
FIG. 3 illustrates the contact angles of CYTOP-M and CYTOP-S treated glass surface compared to the control surface before and after chemical treatment.

FIG. 3 illustrates the contact angles of the CYTOP-M and CYTOP-S treated glass surface compared to the control surface before and after chemical treatment. CYTOP treated glass surface showed a contact angle of about 120 degrees for CYTOP-M and about 123 degrees for CYTOP-S. After the deposition of the norbornene silane layer, the contact angle decreased to 116 degrees for CYTOP-M and 120 degrees for CYTOP-S. Following PAZAM coupling and oligo grafting, the contact angle decreased substantially down to 51 degrees for the CYTOP-M surface, indicating that DNA clusters and the hydrophilic PAZAM polymer bound to the surface and the surface was rendered hydrophilic. In contrast, CYTOP-S surface retained its hydrophobicity with only a slight decrease in contact angle. Due to its chemical inertness and hydrophobic characteristics, CYTOP-S is identified to be a good candidate for surface patterning (e.g. to form interstitial regions between analyte-bearing features).

Figure 4:
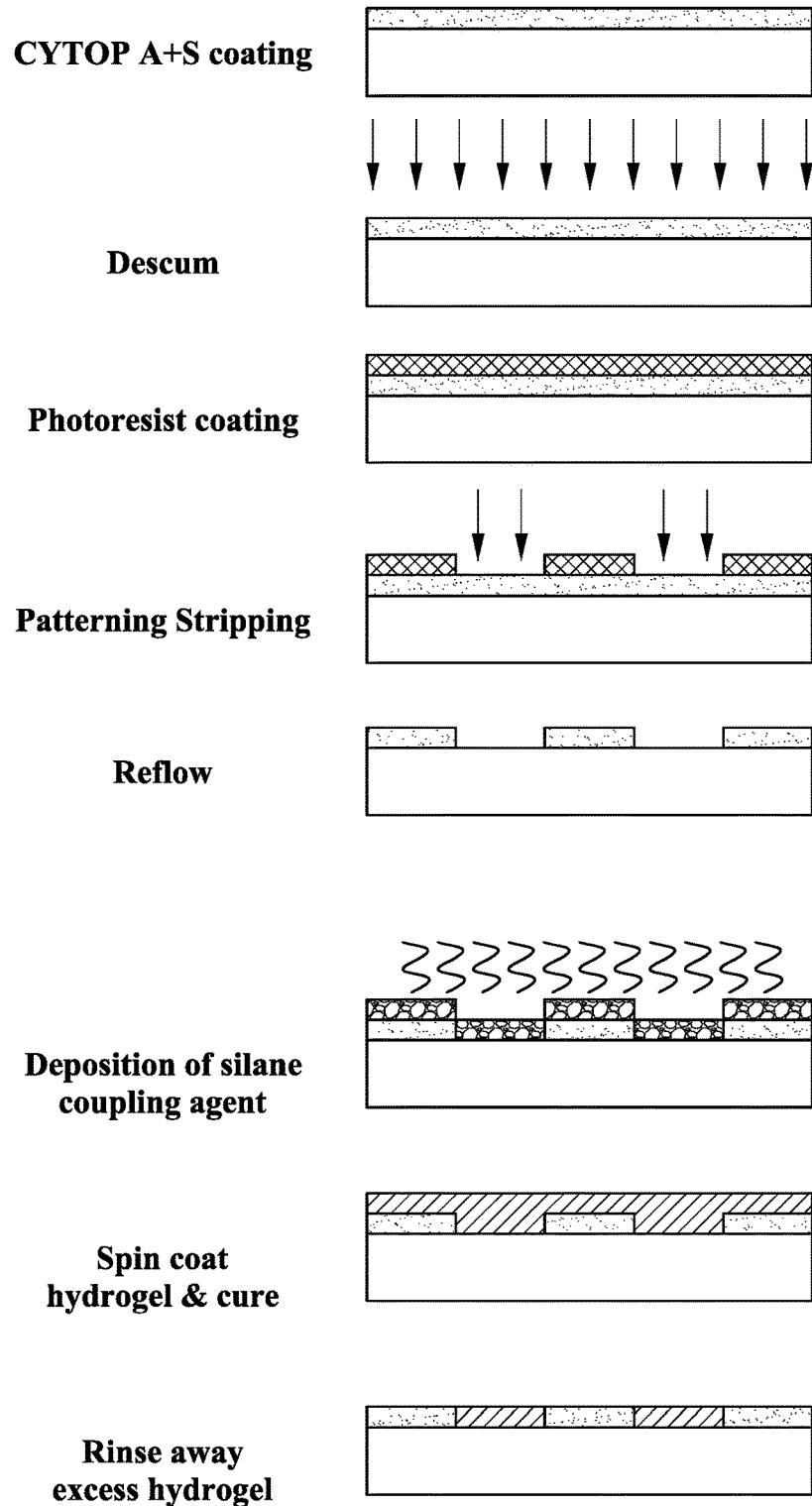
FIG. 4 illustrates a cross-section view of a typical workflow for creating a patterned surface.

A typical workflow is illustrated in FIG. 4 for preparing a patterned surface using CYTOP-S as hydrophobic coating. First, the surface was treated with CYTOP-S. Because CYTOP-S lacks any reactive functional groups to couple to the glass or silicon surface, an adhesion promoting layer may be used to facilitate the coating of CYTOP-S to the surface. In this example, a thin layer of CYTOP-A was first coated to the glass surface. Then, CYTOP-S was coated evenly on the surface. After subsequent curing, the perfluorinated polymers in the two CYTOP layers entangle further to form stronger adhesion. Non-limiting examples of a material that may be used as an adhesion promoting layer for glass or silicon surface also include an amino-based silane coupling agent such as APTMS, APTES, etc.

In this standard workflow, the CYTOP-S surface was treated with oxygen plasma in order to deposit standard photoresist for photolithography. The plasma treatment makes the CYTOP-S more hydrophilic so that the photoresist can be coated on top of it. With this surface modification, standard photoresists tend to dewet from the surface. During the process, the CYTOP-S surface lost its hydrophobicity and chemical inertness after the oxygen plasma treatment. While the hydrophobicity of CYTOP-S surface was recovered via a high temperature reflow step at 180° C. using a CYTOP-S solution, the chemical inertness of the surface was not recovered and non-specific binding of PAZAM to the interstitial CYTOP-S surface was observed.

Reflow Process

Figure 9B:
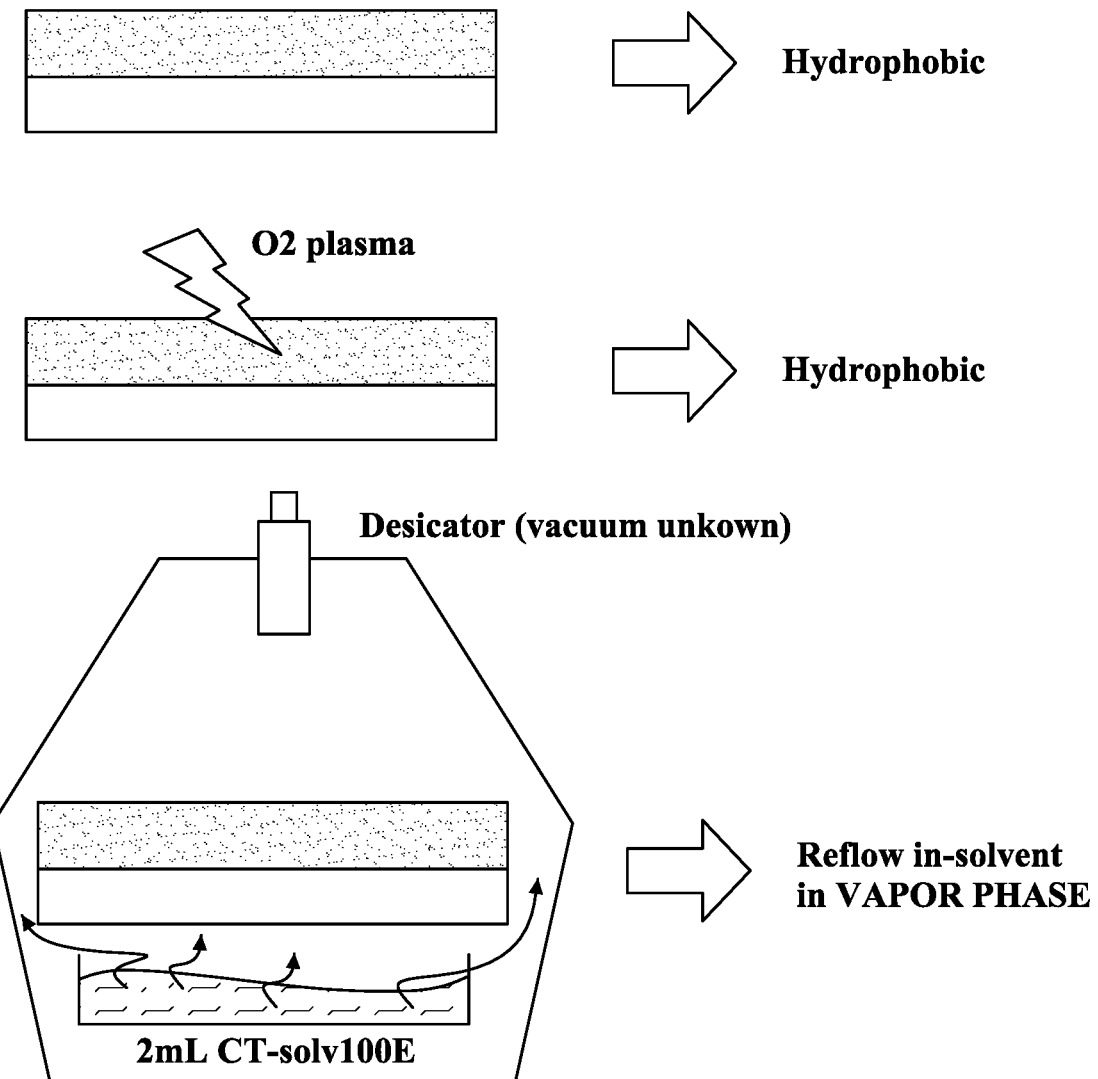
FIG. 9B illustrates an example of a vapor phase reflow process.

In any embodiments of the methods described herein, the methods may further comprise a reflow process to recover damage to the surface during patterning. For example, if the CYTOP-S surface has been damaged (such as loss of inertness or of hydrophobic properties) during the patterning process, CYTOP-S surface properties may be restored by a reflow process using a CYTOP-S containing solvent. The solvent reflow may be conducted either as a liquid phase process as exemplified in FIG. 9A or as a vapor phase process as exemplified in FIG. 9B. Non-limiting examples of a liquid phase reflow include depositing the CYTOP-S solvent on surface or spin coating on the surface directly at a high temperature (for example, 180° C.), then curing at a lower temperature (for example, 50° C.). In the vapor phase reflow, the substrate is placed in a vacuum-sealed desiccator with some amount of CYTOP-S containing solvent in it, such as 2 mL of a perfluorinated fluorocarbon solvent such as CT-SOLV100E. Solvents that may be used in the reflow process include but are not limited to CT-SOLV180, or CT-SOLV100E. Other solvents of choice include Fluorinert™ FC-40, Fluorinert™ FC-770, each of which is capable of dissolving the perfluorinated polymers.

Figure 10A:
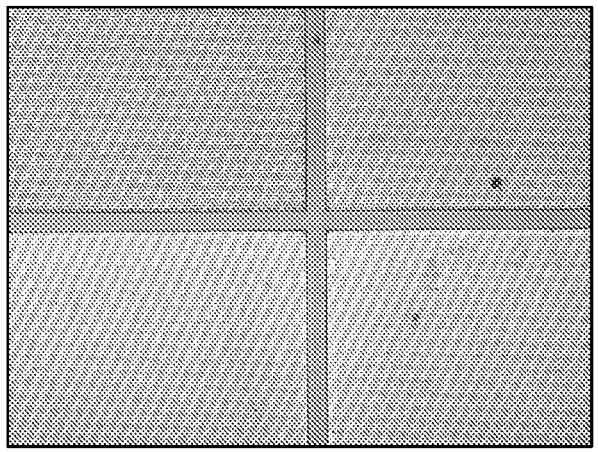
FIG. 10A is an optical microscopy image of PAZAM coated CYTOP-S nanowells (diameter of 700 nm to 1.1 μm) after $O_2$ plasma treatment.
Figure 10B:
FIG. 10B is an optical microscopy image of PAZAM coated CYTOP-S nanowells in FIG. 10A after liquid phase solvent reflow.
Figure 10C:
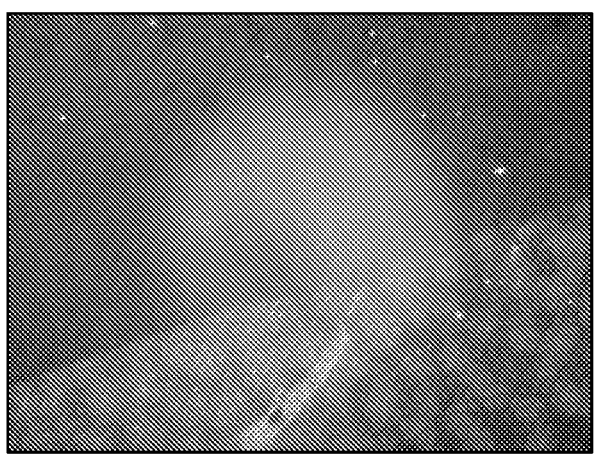
FIG. 10C is a fluorescence image of the PAZAM coated CYTOP-S nanowells of FIG. 10B after the wetting/dewetting of an aqueous droplet with fluorescent die.
Figure 11A:
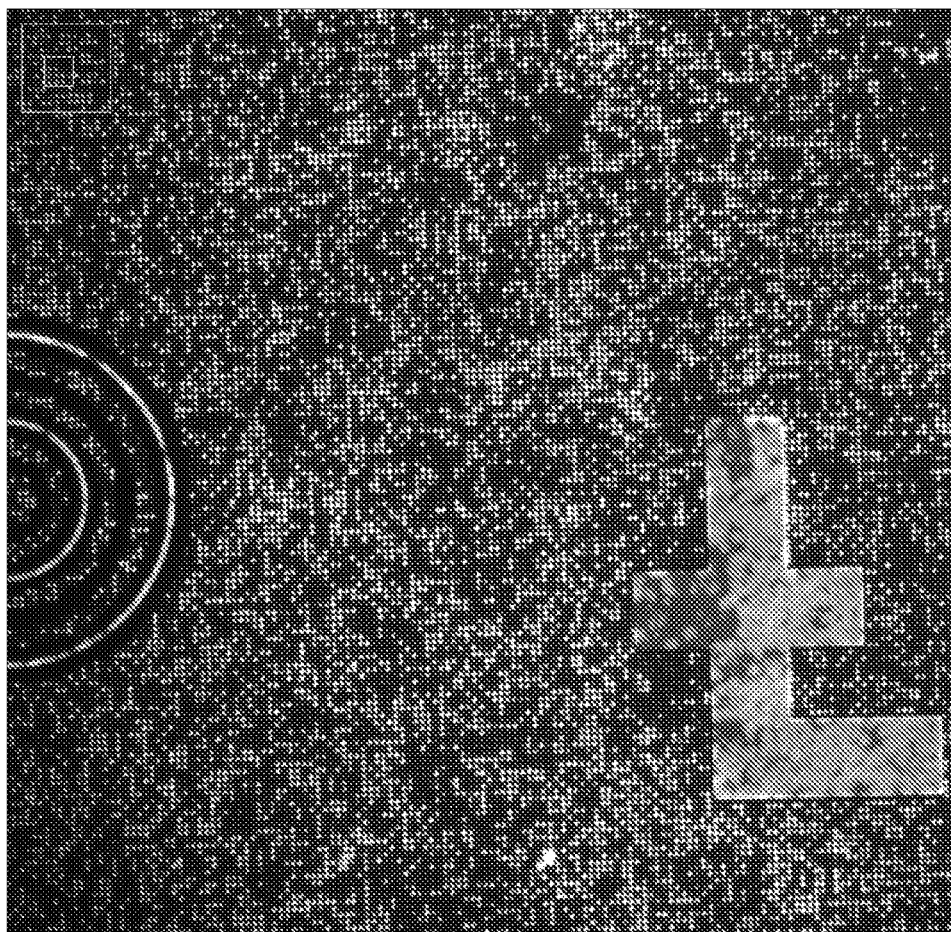
FIG. 11A depicts DNA cluster patterning in sub-micron sized wells. The bright spots are fluorescent dye labeled DNA clusters. In the "t"-shaped area, the material is $SiO_2$ without patterning, and the clusters are randomly distributed. The image was generated using the topology depicted in FIG. 11B.
Figure 11B:
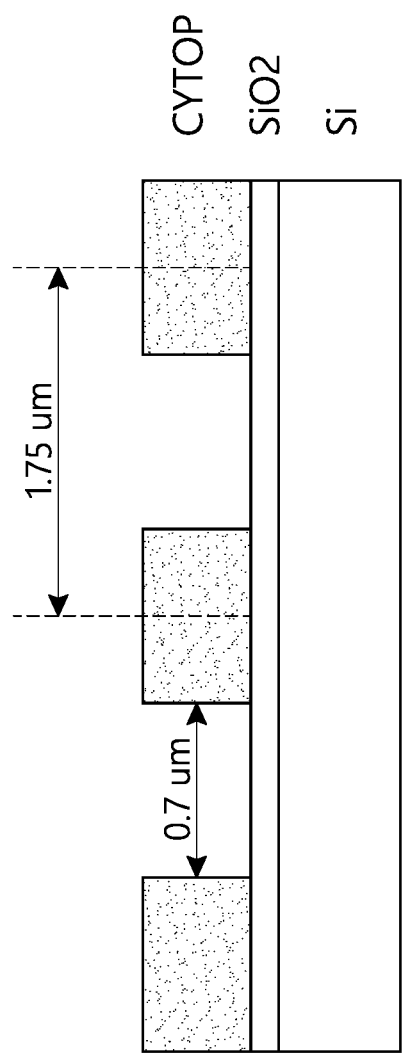
FIG. 11B depicts a cross-sectional illustration for the patterned substrate. The wells have a 0.7 micron diameter arrayed with a 1.75 micro pitch.
Figure 11C:
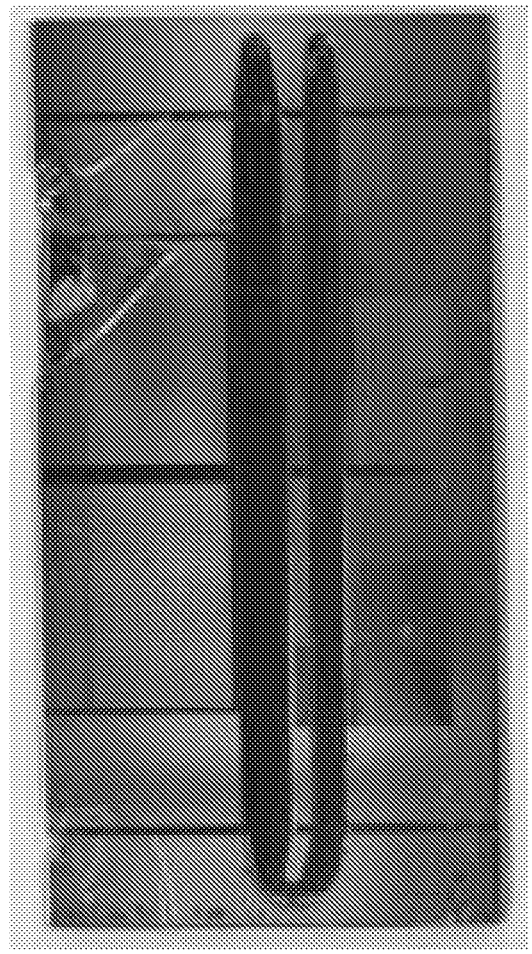
FIG. 11C shows the patterned substrate assembly in a MiSeq® flowcell format to facilitate the exchange of bioreagents. The picture was generated using the topology depicted in FIG. 11B.

In another embodiment, the patterned CYTOP-S surface may be subject to the reflow process after hydrogel coating to restore surface property damage. The reflow process has no impact on the hydrogel quality for sequencing. FIG. 10A is an optical microscopy image of PAZAM coated CYTOP-S nanowells (700 nm to 1.1 μm) after $O_2$ plasma treatment. FIG. 10B is an optical microscopy image of the PAZAM coated CYTOP-S nanowells in FIG. 10A after liquid phase solvent reflow. FIG. 10C is a fluorescence image of the PAZAM coated CYTOP-S nanowells of FIG. 10B after the wetting/dewetting of an aqueous droplet with fluorescent die, indicating that PAZAM is still accessible.

Solid Support

Solid supports that are useful in an apparatus or method of the present disclosure can be a generally flat surface (e.g., a chip or slide) or can have a curved surface (e.g. a cylinder or drum). It can also be two- or three-dimensional. Useful materials include glass, quartz, plastic (such as polystyrene (low cross-linked and high cross-linked polystyrene), polycarbonate, polypropylene or poly(methylmethacrylate)), acrylic copolymer, polyamide, silicon, metal (e.g., alkanethiolate-derivatized gold), cellulose, nylon, latex, dextran, gel matrix (e.g., silica gel), polyacrolein, or composites. In some embodiments, the solid support comprises glass.

Features

The features of an array can have any of a variety of shapes. In some embodiments, the term "feature" also refers to "contours" on a patterned surface when all of a contour serves as a feature in an array. For example, when observed in a two dimensional plane, such as on the surface of an array, the features can appear rounded, circular, oval, rectangular, square, symmetric, asymmetric, triangular, polygonal, or the like. The features can be arranged in a regular repeating pattern including, for example, a square lattice, rectangular lattice, rhombic lattice, hexagonal lattice or oblique lattice. A pattern can be selected to achieve a desired level of packing. For example, round features are optimally packed in a hexagonal arrangement. Of course other packing arrangements can also be used for round features and vice versa.

The size of a feature on an array (or other object used in a method or system herein) can be selected to suit a particular application. For example, in some embodiments a feature of an array can have a size that accommodates only a single nucleic acid molecule. A surface having a plurality of features in this size range is useful for constructing an array of molecules for detection at single molecule resolution. Features in this size range are also useful for use in arrays having features that each contain a colony of nucleic acid molecules. Thus, the features of an array can each have an area that is no larger than about 1 $mm^2$, no larger than about 500 $\mu m^2$, no larger than about 100 $\mu m^2$, no larger than about 10 $\mu m^2$, no larger than about 1 $\mu m^2$, no larger than about 500 $nm^2$, or no larger than about 100 $nm^2$, no larger than about 10 $nm^2$, no larger than about 5 $nm^2$, or no larger than about 1 $nm^2$. Alternatively or additionally, the features of an array will be no smaller than about 1 $mm^2$, no smaller than about 500 $\mu m^2$, no smaller than about 100 $\mu m^2$, no smaller than about 10 $\mu m^2$, no smaller than about 1 $\mu m^2$, no smaller than about 500 $nm^2$, no smaller than about 100 $nm^2$, no smaller than about 10 $nm^2$, no smaller than about 5 $nm^2$, or no smaller than about 1 $nm^2$. Indeed, a feature can have a size that is in a range between an upper and lower limit selected from those exemplified above. Although several size ranges for features of a surface have been exemplified with respect to nucleic acids and on the scale of nucleic acids, it will be understood that features in these size ranges can be used for applications that do not include nucleic acids. It will be further understood that the size of the features need not necessarily be confined to a scale used for nucleic acid applications.

An array can also be characterized with regard to pitch. For example, the size of the features and/or pitch of the features can vary such that arrays can have a desired density. For example, the average feature pitch can be at most 100 µm, 50 µm, 10 µm, 5 µm, 1 µm, 0.5 µm, 0.4 µm, 0.3 µm, 0.2 µm, 0.1 µm or less. Alternatively or additionally, the average feature pitch can be at least 0.1 µm, 0.2 µm, 0.3 µm, 0.4 µm, 0.5 µm, 1 µm, 5 µm, 10 µm, 50 µm, 100 µm or more. Similarly, the maximum feature pitch can be at most 100 µm, 50 µm, 10 µm, 5 µm, 1 µm, 0.5 µm 0.4 µm, 0.3 µm, 0.2 µm, 0.1 µm or less; and/or the minimum feature pitch can be at least 0.1 µm, 0.2 µm, 0.3 µm, 0.4 µm, 0.5 µm, 1 µm, 5 µm, 10 µm, 50 µm, 100 µm or more. The above ranges can apply to the average, maximum or minimum pitch between features.

The density of features in an array can also be understood in terms of the number of features present per unit area. For example, the average density of features for an array can be at least about $1\times10^3$ features/mm$^2$, $1\times10^4$ features/mm$^2$, $1\times10^5$ features/mm$^2$, $1\times10^6$ features/mm$^2$, $1\times10^7$ features/mm$^2$, $1\times10^8$ features/mm$^2$, or $1\times10^9$ features/mm$^2$ or higher. Alternatively or additionally the average density of features for an array can be at most about $1\times10^9$ features/mm$^2$, $1\times10^8$ features/mm$^2$, $1\times10^7$ features/mm$^2$, $1\times10^6$ features/mm$^2$, $1\times10^5$ features/mm$^2$, $1\times10^4$ features/mm$^2$, or $1\times10^3$ features/mm$^2$ or less.

An array having a regular pattern of features can be ordered with respect to the relative locations of the features but random with respect to one or more other characteristic of each feature. For example, in the case of a nucleic acid array, the nucleic acid features can be ordered with respect to their relative locations but random with respect to one's knowledge of the sequence for the nucleic acid species present at any particular feature. As a more specific example, nucleic acid arrays formed by seeding a repeating pattern of features with template nucleic acids and amplifying the template at each feature to form copies of the template at the feature (e.g., via cluster amplification or bridge amplification) will have a regular pattern of nucleic acid features, as determined by the position of the contours that form the features, but will be random with regard to the distribution of sequences of the nucleic acids across the array. Thus, detection of the presence of nucleic acid material generally on the array can yield a repeating pattern of features, whereas sequence specific detection can yield non-repeating distribution of signals across the array.

In some embodiments, the methods described herein form contours with a single repeating pattern. In some other embodiments, the methods described herein form contours with multiple repeating patterns, providing arrays with at least a first repeating pattern of features and a second repeating pattern of features. In some such embodiments, the first and second patterns form an interleaved pattern along the exterior surface, wherein the features of the first repeating pattern occur at a first elevation and the features of the second repeating pattern occur at a second elevation, and wherein the features include attachment points for analytes, whereby the features of the first repeating pattern are configured to attach analytes at a different elevation relative to analytes attached to the features of the second repeating pattern. Examples of substrates having contours with multiple repeating patterns that can be made or used in a method or composition set forth herein are described in PCT Appln. No. PCT/US2017/024578, filed Mar. 28, 2017, and titled "Multi-Plane Microarrays" which is hereby incorporated by reference in its entirety.

Analytical Applications

Some embodiments are directed to methods of detecting an analyte using a substrate with a patterned surface prepared by the methods described herein. In some embodiments, the analyte is selected from nucleic acids, polynucleotides, proteins, antibodies, epitopes to antibodies, enzymes, cells, nuclei, cellular organelles, or small molecule drugs. In one embodiment, the analyte is a polynucleotide. In one embodiment, the detecting includes determining a nucleotide sequence of the polynucleotide.

Some embodiments described herein are related to methods of preparing an array of polynucleotides, the methods include providing a solid support comprising a patterned surface, the surface comprising microscale and/or nanoscale contours coated with a gel material that is capable of covalently bonding to oligonucleotides, the surface is prepared by any of the methods described herein; and covalently attaching a plurality of first oligonucleotides and a plurality of second oligonucleotides to the gel material. In some embodiments, the methods further include contacting the plurality of first oligonucleotides attached to the polymer coating with templates to be amplified, each template comprising at the 3' end a sequence capable of hybridizing to the first oligonucleotides and at the 5' end a sequence the complement of which is capable of hybridizing to the second oligonucleotides. In some embodiments, the methods further include amplifying the templates using the first oligonucleotides and the second oligonucleotides, thereby generating a clustered array of polynucleotides.

Some embodiments that use nucleic acids can include a step of amplifying the nucleic acids on the substrate. Many different DNA amplification techniques can be used in conjunction with the substrates described herein. Exemplary techniques that can be used include, but are not limited to, polymerase chain reaction (PCR), rolling circle amplification (RCA), multiple displacement amplification (MDA), or random prime amplification (RPA). In particular embodiments, one or more primers used for amplification can be attached to a substrate (e.g. via a gel or polymer coating). In PCR embodiments, one or both of the primers used for amplification can be attached to the substrate. Formats that utilize two species of attached primer are often referred to as bridge amplification because double stranded amplicons form a bridge-like structure between the two attached primers that flank the template sequence that has been copied. Exemplary reagents and conditions that can be used for bridge amplification are described, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420, each of which is incorporated herein by reference.

PCR amplification can also be carried out with one amplification primer attached to a substrate and a second primer in solution. An exemplary format that uses a combination of one attached primer and soluble primer is emulsion PCR as described, for example, in Dressman et al., Proc. Natl. Acad. Sci. USA 100:8817-8822 (2003), WO 05/010145, or U.S. Patent Publ. Nos. 2005/0130173 or 2005/0064460, each of which is incorporated herein by reference. Emulsion PCR is illustrative of the format and it will be understood that for purposes of the methods set forth herein the use of an emulsion is optional and indeed for several embodiments an emulsion is not used. Furthermore, primers need not be attached directly to substrate or solid supports as set forth in the ePCR references and can instead be attached to a gel or polymer coating as set forth herein.

RCA techniques can be modified for use in a method of the present disclosure. Exemplary components that can be used in an RCA reaction and principles by which RCA produces amplicons are described, for example, in Lizardi et al., *Nat. Genet.* 19:225-232 (1998) and US 2007/0099208 A1, each of which is incorporated herein by reference. Primers used for RCA can be in solution or attached to a gel or polymer coating.

MDA techniques can be modified for use in a method of the present disclosure. Some basic principles and useful conditions for MDA are described, for example, in Dean et al., *Proc Natl. Acad. Sci. USA* 99:5261-66 (2002); Lage et al., *Genome Research* 13:294-307 (2003); Walker et al., *Molecular Methods for Virus Detection*, Academic Press, Inc., 1995; Walker et al., *Nucl. Acids Res.* 20:1691-96 (1992); U.S. Pat. Nos. 5,455,166; 5,130,238; and 6,214,587, each of which is incorporated herein by reference. Primers used for MDA can be in solution or attached to a gel or polymer coating.

In particular embodiments a combination of the above-exemplified amplification techniques can be used. For example, RCA and MDA can be used in a combination wherein RCA is used to generate a concatameric amplicon in solution (e.g. using solution-phase primers). The amplicon can then be used as a template for MDA using primers that are attached to a substrate (e.g. via a gel or polymer coating). In this example, amplicons produced after the combined RCA and MDA steps will be attached to the substrate.

Substrates of the present disclosure that contain nucleic acid arrays can be used for any of a variety of purposes. A particularly desirable use for the nucleic acids is to serve as capture probes that hybridize to target nucleic acids having complementary sequences. The target nucleic acids once hybridized to the capture probes can be detected, for example, via a label recruited to the capture probe. Methods for detection of target nucleic acids via hybridization to capture probes are known in the art and include, for example, those described in U.S. Pat. Nos. 7,582,420; 6,890, 741; 6,913,884 or 6,355,431 or U.S. Pat. Pub. Nos. 2005/0053980 A1; 2009/0186349 A1 or 2005/0181440 A1, each of which is incorporated herein by reference. For example, a label can be recruited to a capture probe by virtue of hybridization of the capture probe to a target probe that bears the label. In another example, a label can be recruited to a capture probe by hybridizing a target probe to the capture probe such that the capture probe can be extended by ligation to a labeled oligonucleotide (e.g., via ligase activity) or by addition of a labeled nucleotide (e.g. via polymerase activity).

In some embodiments, a substrate described herein can be used for determining a nucleotide sequence of a polynucleotide. In such embodiments, the method can comprise the steps of (a) contacting a polynucleotide polymerase with polynucleotide clusters attached to a surface of a substrate (e.g., via any one of the polymer or gel coatings described herein); (b) providing nucleotides to the surface of the substrate such that a detectable signal is generated when one or more nucleotides are utilized by the polynucleotide polymerase; (c) detecting signals at one or more attached polynucleotide (or one or more clusters produced from the attached polynucleotides); and (d) repeating steps (b) and (c), thereby determining a nucleotide sequence of a substrate-attached polynucleotide.

Nucleic acid sequencing can be used to determine a nucleotide sequence of a polynucleotide by various processes known in the art. In a preferred method, sequencing-by-synthesis (SBS) is utilized to determine a nucleotide sequence of a polynucleotide attached to a surface of a substrate (e.g. via any one of the polymer coatings described herein). In such a process, one or more nucleotides are provided to a template polynucleotide that is associated with a polynucleotide polymerase. The polynucleotide polymerase incorporates the one or more nucleotides into a newly synthesized nucleic acid strand that is complementary to the polynucleotide template. The synthesis is initiated from an oligonucleotide primer that is complementary to a portion of the template polynucleotide or to a portion of a universal or non-variable nucleic acid that is covalently bound at one end of the template polynucleotide. As nucleotides are incorporated against the template polynucleotide, a detectable signal is generated that allows for the determination of which nucleotide has been incorporated during each step of the sequencing process. In this way, the sequence of a nucleic acid complementary to at least a portion of the template polynucleotide can be generated, thereby permitting determination of the nucleotide sequence of at least a portion of the template polynucleotide.

Flow cells provide a convenient format for housing an array that is produced by the methods of the present disclosure and that is subjected to a sequencing-by-synthesis (SBS) or other detection technique that involves repeated delivery of reagents in cycles. For example, to initiate a first SBS cycle, one or more labeled nucleotides, DNA polymerase, etc., can be flowed into/through a flow cell that houses a nucleic acid array made by methods set forth herein. Those sites of an array where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with an array produced by the methods of the present disclosure are described, for example, in Bentley et al., *Nature* 456: 53-59 (2008), WO 04/018497; U.S. Pat. No. 7,057,026; WO 91/06678; WO 07/123744; U.S. Pat. Nos. 7,329,492; 7,211, 414; 7,315,019; 7,405,281, and US 2008/0108082, each of which is incorporated herein by reference in its entirety.

In some embodiments of the above-described method, which employ a flow cell, only a single type of nucleotide is present in the flow cell during a single flow step. In such embodiments, the nucleotide can be selected from the group consisting of dATP, dCTP, dGTP, dTTP, and analogs thereof. In other embodiments of the above-described method which employ a flow cell, a plurality different types of nucleotides are present in the flow cell during a single flow step. In such methods, the nucleotides can be selected from dATP, dCTP, dGTP, dTTP, and analogs thereof.

Determination of the nucleotide or nucleotides incorporated during each flow step for one or more of the polynucleotides attached to the polymer coating on the surface of the substrate present in the flow cell is achieved by detecting a signal produced at or near the polynucleotide template. In some embodiments of the above-described methods, the detectable signal comprises an optical signal. In other embodiments, the detectable signal comprises a non-optical signal. In such embodiments, the non-optical signal comprises a change in pH at or near one or more of the polynucleotide templates.

Applications and uses of substrates of the present disclosure have been exemplified herein with regard to nucleic acids. However, it will be understood that other analytes can be attached to a substrate set forth herein and analyzed. One or more analytes can be present in or on a substrate of the present disclosure. The substrates of the present disclosure are particularly useful for detection of analytes, or for carrying out synthetic reactions with analytes. Thus, any of a variety of analytes that are to be detected, characterized, modified, synthesized, or the like can be present in or on a substrate set forth herein. Exemplary analytes include, but are not limited to, nucleic acids (e.g., DNA, RNA or analogs thereof), proteins, polysaccharides, cells, antibodies, epitopes, receptors, ligands, enzymes (e.g., kinases, phosphatases or polymerases), small molecule drug candidates, or the like. A substrate can include multiple different species from a library of analytes. For example, the species can be different antibodies from an antibody library, nucleic acids having different sequences from a library of nucleic acids, proteins having different structure and/or function from a library of proteins, drug candidates from a combinatorial library of small molecules, etc.

In some embodiments, analytes can be distributed to features on a substrate such that they are individually resolvable. For example, a single molecule of each analyte can be present at each feature. Alternatively, analytes can be present as colonies or populations such that individual molecules are not necessarily resolved. The colonies or populations can be homogenous with respect to containing only a single species of analyte (albeit in multiple copies). Taking nucleic acids as an example, each feature on a substrate can include a colony or population of nucleic acids and every nucleic acid in the colony or population can have the same nucleotide sequence (either single stranded or double stranded). Such colonies can be created by cluster amplification or bridge amplification as set forth previously herein. Multiple repeats of a target sequence can be present in a single nucleic acid molecule, such as a concatamer created using a rolling circle amplification procedure. Thus, a feature on a substrate can contain multiple copies of a single species of an analyte. Alternatively, a colony or population of analytes that are at a feature can include two or more different species. For example, one or more wells on a substrate can each contain a mixed colony having two or more different nucleic acid species (i.e. nucleic acid molecules with different sequences). The two or more nucleic acid species in a mixed colony can be present in non-negligible amounts, for example, allowing more than one nucleic acid to be detected in the mixed colony.

EXAMPLES

Additional embodiments are disclosed in further detail in the following examples, which are not in any way intended to limit the scope of the claims.

Example 1

FIG. 5 is a workflow diagram of an example process for preparing a patterned surface using CYTOP-S that was conducted. As described above, the oxygen plasma treatment of CYTOP-S surface was found to result in loss of the hydrophobicity and chemical inertness of the CYTOP layer. It was discovered that certain photoresists, such as Shipley 18 series photoresists, can be directly spun on the CYTOP-S coated surface without requiring any oxygen plasma treatment.

Surface Preparation: First, the substrate (glass substrate or silicon dioxide coated Si substrate) was cleaned with isopropyl alcohol (IPA), deionized water (DI) and then blown dry with nitrogen gas. Then, the substrate was placed in a vacuum desiccator at 60° C. for 12 hours for silanization with APTMS. Then, 0.5% CYTOP-A coating solution was spun-coated on the substrate surface at 2000 rpm for 20 seconds. The coated substrate was soft-baked at 50° C. for 30 min. Subsequently, 5% CYTOP-S coating solution was spun-coated on to CYTOP-A layer at 1000 rpm for 30 seconds. To prepare the CYTOP-A and CYTOP-S solutions, a fluorocarbon-based solvent such as the CT-SOLV180 from AGC was used. The substrate was dried at room temperature for 30 min, and then baked at 50° C. for 30 min, followed by 80° C. for 30 min, and finally baked at 250° C. for 30 min. The CYTOP-A/S coating was complete and the substrate was ready for photolithography.

Photolithography: Shipley S1800 photoresist was directly spun coated over the CYTOP layer of the substrate surface (e.g., 3000 rpm for 30 seconds to coat Shipley S1805 with a thickness of 0.5 μm). The substrate was soft-baked at 115° C. for 60 seconds. Either contact aligners or steppers with G-line UV may be used for photolithography with exposure energy around 120 mJ/cm$^2$. The development process was conducted by putting the substrates into Microposit MF-321 developer for 60 sec, then rinsing with deionized water followed by nitrogen gas blow dry. The Shipley S18 photoresist patterned substrate was then hard-baked in 120° C. oven for 30 min. To etch away the CYTOP in the well area to expose the underneath SiO$_2$ surface, the substrate was treated with O$_2$ plasma (Parallel Plate Plasma Etcher, 100 sccm O$_2$ flux, 150 W, 180 sec dry etch). The resulting surface of the substrate comprised patterned, exposed SiO$_2$ surface separated by interstitial regions covered by CYTOP-S, ready for the hydrogel patterning steps.

Hydrogel Patterning: a silane coupling agent was deposited on the treated surface of the substrate, covering both the exposed SiO$_2$ surface and the interstitial regions covered by CYTOP-S. Then hydrogel was spun-coated over the silane coupling agent to form covalent bonding such that the hydrogel was immobilized on the surface. After curing, the excess hydrogel was rinsed away. The hydrogel patterned surface can be directly used in oligo grafting without polishing.

Figures 6A, 6B:
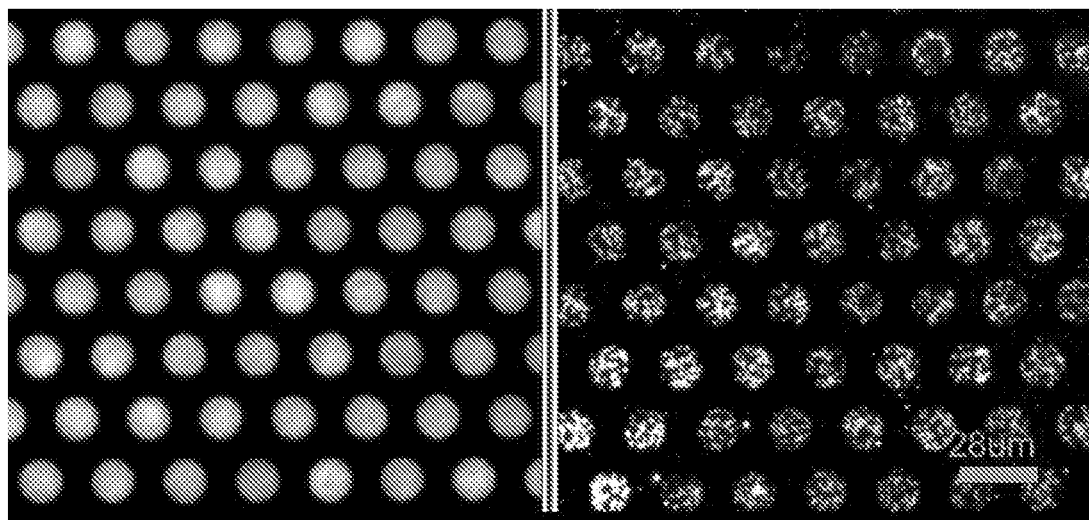
FIGS. 6A and 6B are fluorescent images of a patterned device surface with 14 μm microwells.

FIGS. 6A and 6B are fluorescent images of a patterned device surface containing 14 μm microwells with 28 μm pitch before and after clustering and 14 cycle sequencing. The device surface was prepared according to the Shipley photoresist workflow described in FIG. 5 using Shipley S1805 with a total thickness of 370 nm for the combined CYTOP-A and CYTOP-S layer. FIG. 6A illustrates the image of a PAZAM patterned surface grafted with oligo primers labeled with TET dye. FIG. 6B illustrates the growth of DNA clusters in microwells labeled with SYTOX® intercalating dye. It is clear from these images that there is no sign of non-specific binding of primer or DNA clusters in the hydrophobic CYTOP-S interstitial regions between the microwells.

Figure 6C:
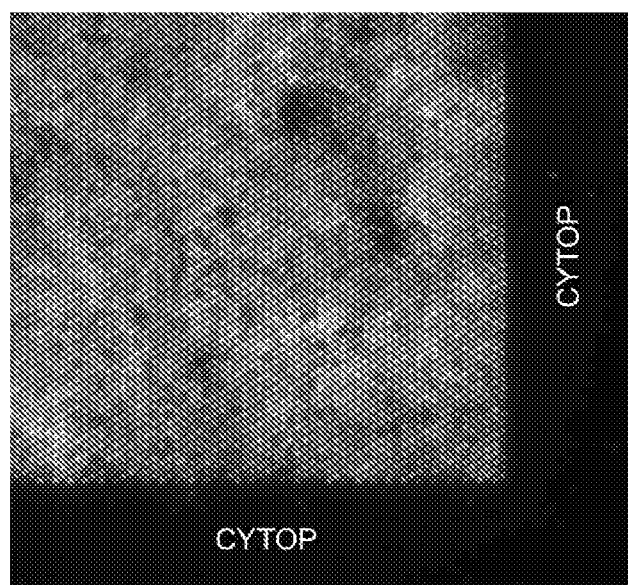
FIG. 6C is a fluorescent image of patterned DNA clusters in 700 nm diameter microwells.

The process was replicated on devices containing 700 nm microwells with 1.8 μm pitch that were fabricated using the same Shipley 18 photoresist workflow described in FIG. 5. FIG. 6C is a fluorescent image of patterned DNA clusters in 700 nm microwells visualized by SYTOX® intercalator dye. Again, the image showed very clean CYTOP-S interstitial regions.

Example 2

In this example, two processes of creating a patterned surface using standard photoresist without the need of oxygen plasma treatment of the surface prior to photolithography were carried out—a direct patterning process and a lift-off process.

Figure 7:
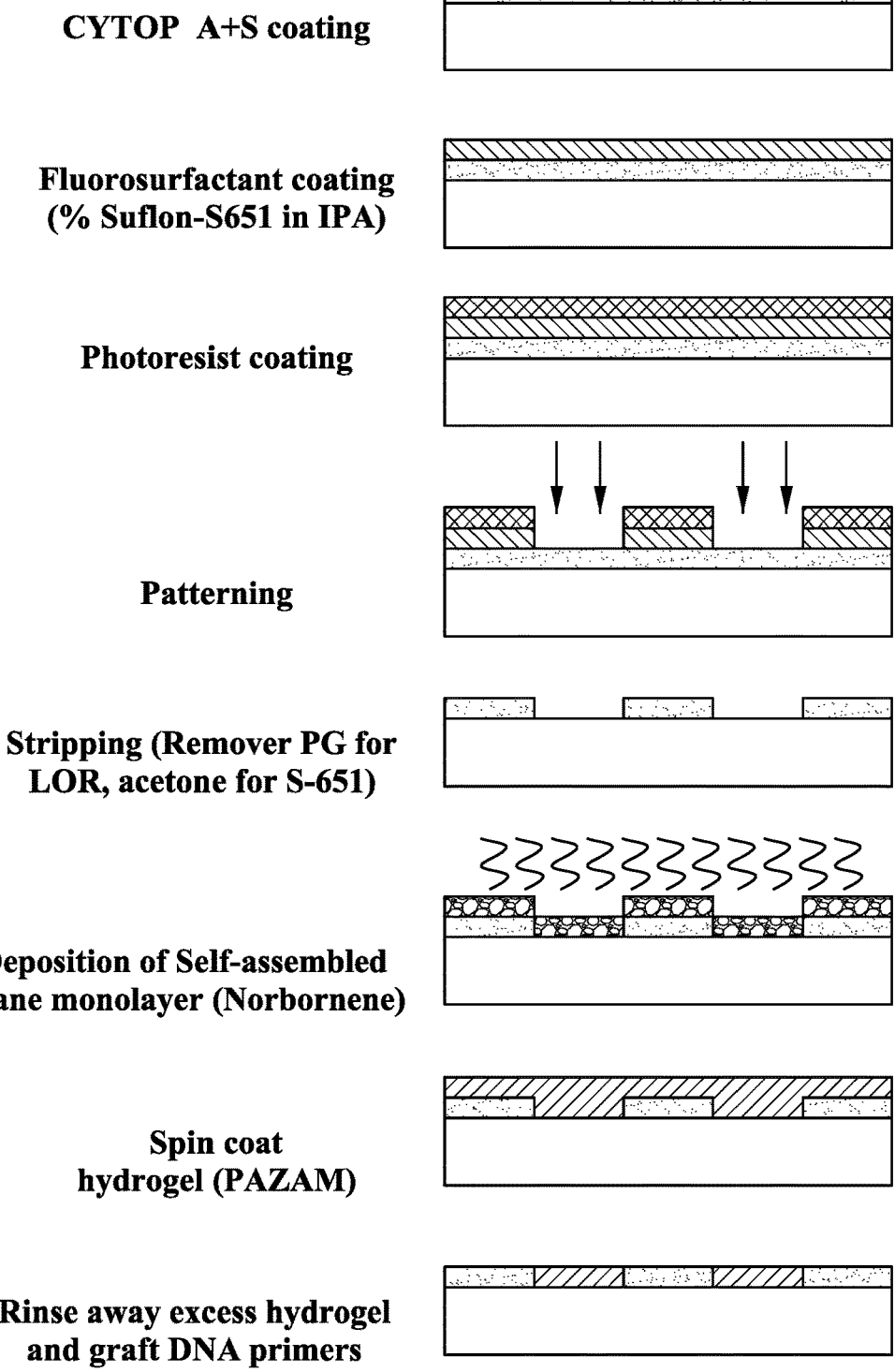
FIG. 7 illustrates one embodiment of an improved direct patterning workflow for creating a patterned surface.

FIG. 7 illustrates a direct patterning workflow for creating a patterned surface.

Surface Preparation: First, CYTOP-A and CYTOP-S were coated onto to a surface of a solid support following the same procedure as described in Example 1. Then, a fluorosurfactant Suflon-5651 was mixed with isopropanol (IPA) to form 1% solution and spun-coated over the CYTOP-S surface at 500 rpm for 5 seconds and then 4000 rpm for 50 seconds. This step reduced the mismatch in surface energy between the CYTOP layer and the photoresist layer to be deposited above it. Subsequently, LOR resist from MICROCHEM was directly spun over the treated surface without requiring any oxygen plasma treatment. This approach expands the process workflow to enable the use of a large variety of photoresists that are used in the fabrication facilities beyond Shipley 18 photoresists. The subsequent steps in this workflow include photoresist coating, soft-baking, UV alignment/exposure, and developing as appropriate for a given photoresist product. To etch away the CYTOP polymer in the well regions to expose the underneath $SiO_2$ area, the substrate was treated with $O_2$ plasma (Parallel Plate Plasma Etcher, 100 sccm $O_2$ flux, 150 W, 180 sec dry etch). The resulting surface of the substrate comprised patterned exposed $SiO_2$ surface separated by hydrophobic interstitial regions, ready for the hydrogel patterning steps.

Direct patterning: First, the photoresist remaining on the substrate surface was removed by sonicating the substrate in acetone for 10 min, following with IPA rinse, water rinse, and then air blow dry. Alternatively, photoresist LOR may be stripped by MICROCHEM Remover PG and then Suflon-S651 may be stripped by acetone. The removal of the photoresist and the fluorosurfactant exposed the underlying CYTOP-S coating as the interstitial regions. Subsequently, the substrate was placed in a vacuum desiccator at 60° C. for 12 hours for norbornene silanization. After the silanization was complete, the substrate was then coated with PAZAM and incubated in 60° C. oven for 1 hour. The excess hydrogel was rinsed away with DI water. The substrate was then sonicated in DI water at 45° C. for 30 min to remove the excess hydrogel that loosely remained on the surface without covalent bonding. The resulting substrate will have hydrogel coated in the well area and clean CYTOP interstitial area free of hydrogel. The substrate is ready for the following primer grafting and DNA seeding and sequencing.

FIG. 8A illustrates a lift-off patterning workflow for creating a patterned surface. The substrate fabrication process was the same as that described above in the workflow exemplified in FIG. 7. After CYTOP and Surflon coating and photolithography, the patterned surface was etched to expose the underlying $SiO_2$ surface in the wells. Then, the patterned substrate with photoresist layer remaining on the surface was directly put in a vacuum desiccator at 60° C. for 12 hours for norbornene silanization. The substrate was then coated with PAZAM and incubated in 60° C. oven for 1 hour. The excess hydrogel was rinsed away with DI water. The substrate was then sonicated in DI water at 45° C. for 30 min to remove hydrogel that loosely remained on the surface without covalent bonding. Subsequently, the substrate was sonicated in acetone at 45° C. for 30 min to remove the photoresist layer at the interstitial regions. The hydrogel deposited on top of the photoresist layer was also removed at the same time. The clean CYTOP surface at the interstitial regions was exposed. The resulting substrate has hydrogel immobilized in the well areas and clean CYTOP interstitial regions free of hydrogel. The substrate is then ready for the following primer grafting and DNA seeding and sequencing.

Figure 8B:
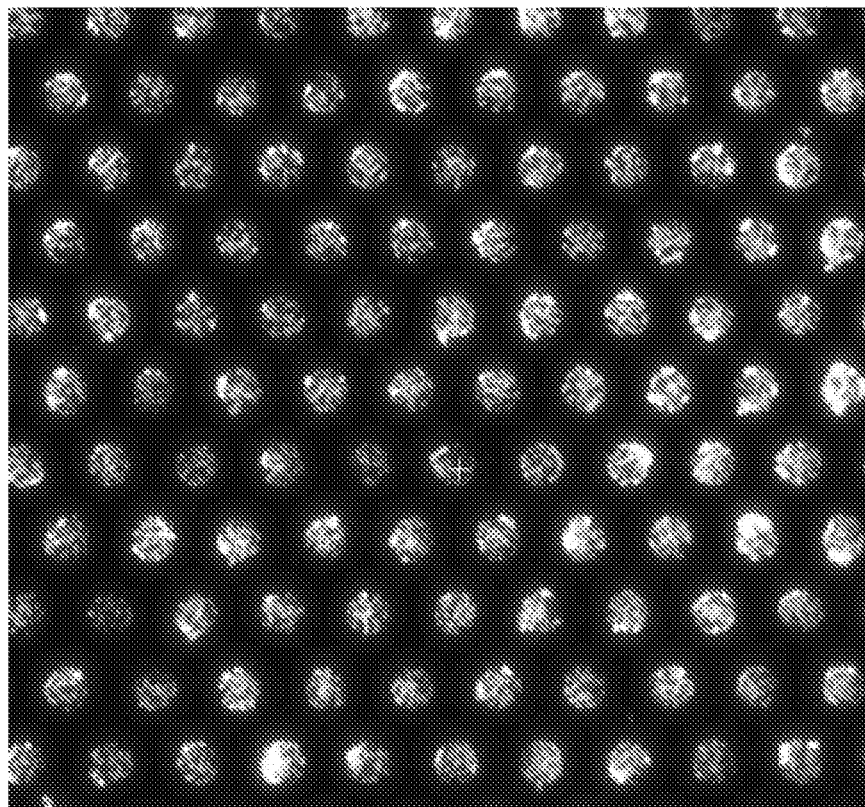
FIG. 8B illustrate a fluorescent image of patterned PAZAM and DNA clusters in 14 diameter μm microwell structures using the lift-off workflow exemplified in FIG. 8A.

FIG. 8B illustrates a fluorescent image of patterned PAZAM and DNA clusters in 14 μm microwell structures using the lift-off workflow exemplified in FIG. 8A. DNA clusters were stained with SYTOX® Intercalator dye. The image suggests that the hydrogel patterning result is comparable to that achieved with the directing patterning workflow in FIG. 7.

In addition, the CYTOP-S surface resumed surface hydrophobicity after the hydrogel patterning in both direct and lift-off processes, with the lift-off method retaining better surface hydrophobicity compared to the direct patterning method.

Example 3

Figure 13A:
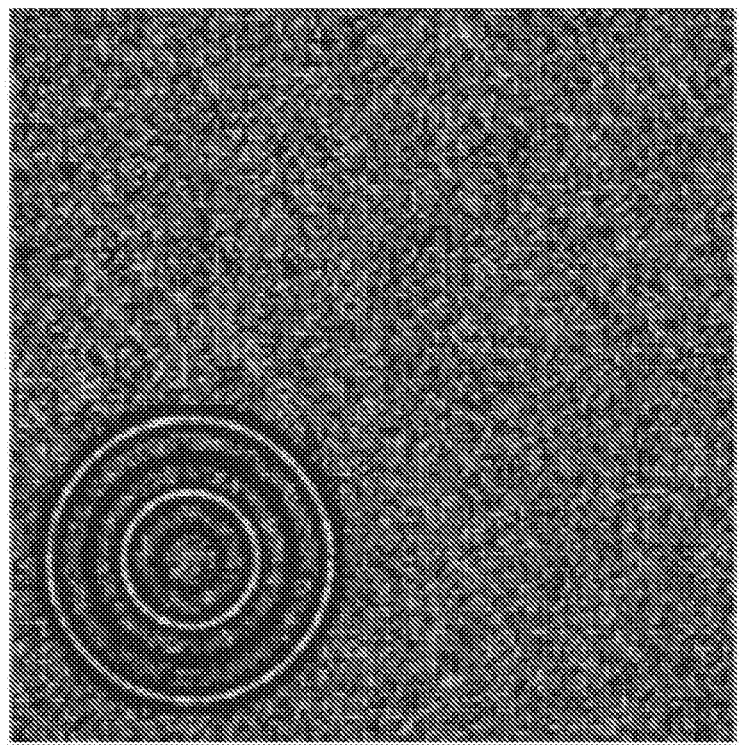
FIGS. 13A-13C show the sequencing results from the CYTOP patterned surface (well diameter 0.7 micron; pitch 1.75 micron).
Figure 13B:
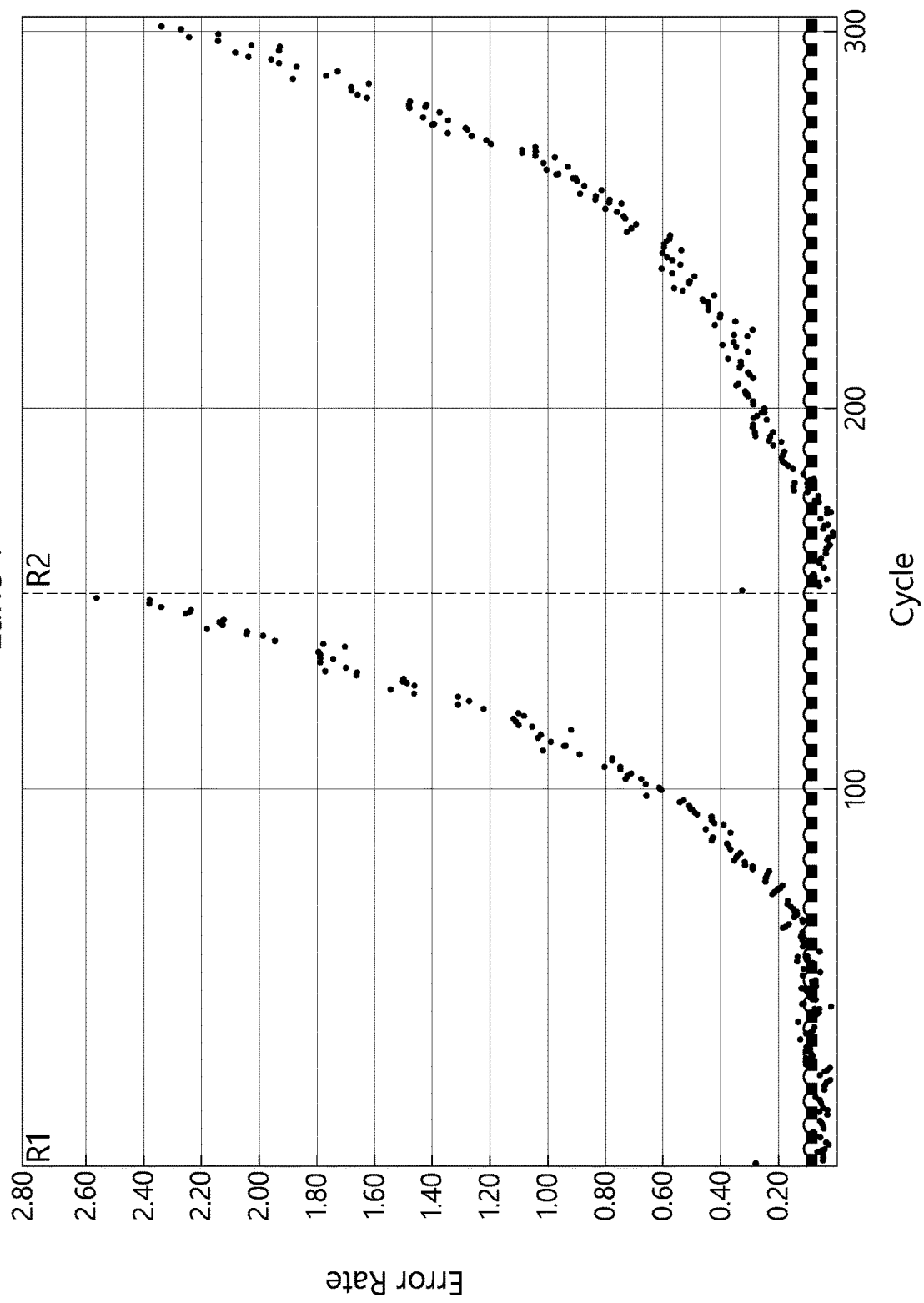
Figure 13C:
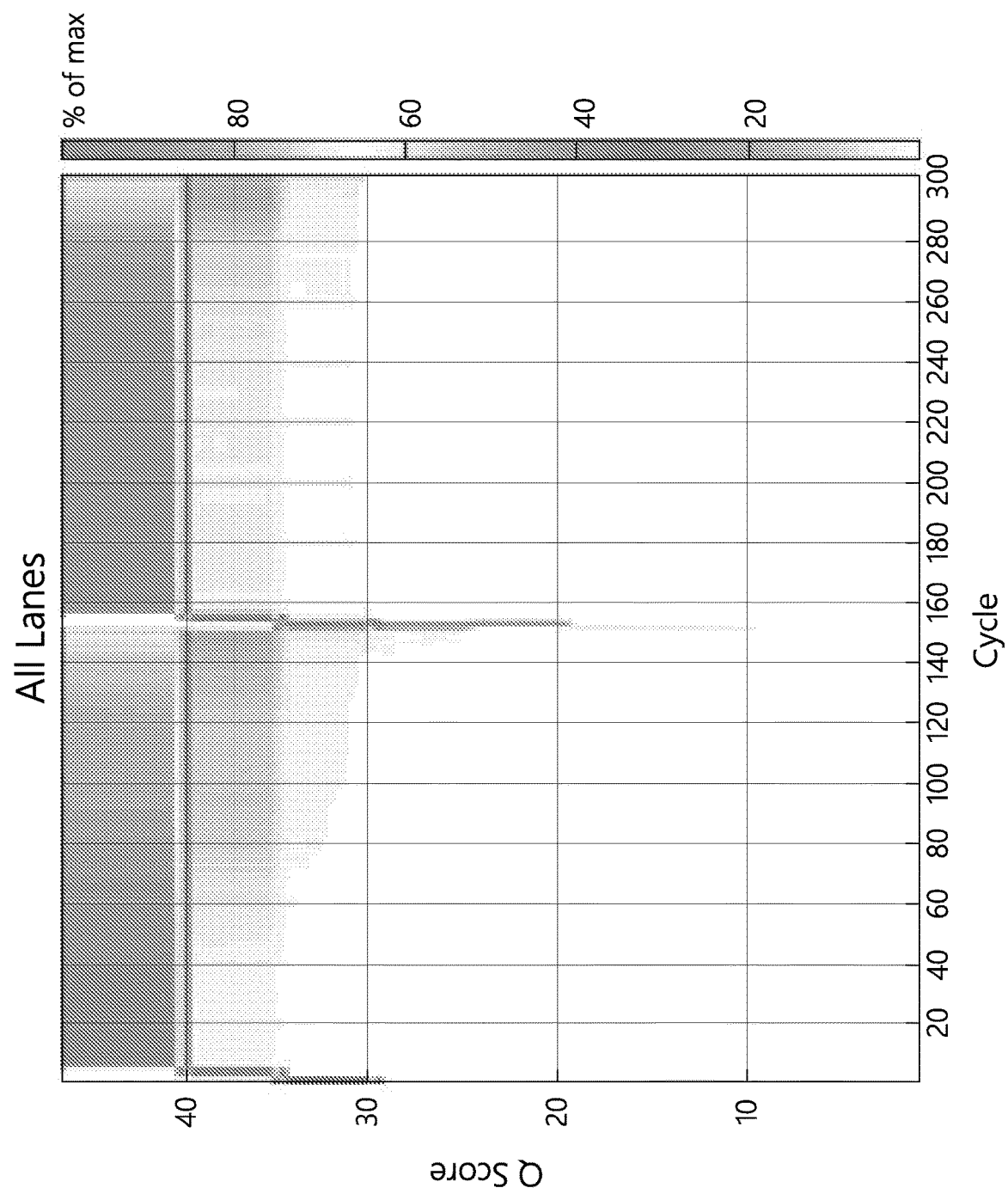

Patterned flow cells with a CYTOP A surface and various well patterns were prepared as described herein. Amplification of DNA sequences was performed using ExAmp amplification methods and 2×150 cycle run. Incubation was run for 1 min, and 15 sec for deblocking, and reactions were run at 65 uL volumes. The following results were obtained, and results are shown in FIGS. 13A-13C.

| Well Size | Cluster PF (%) | Phas/Prephas (%) | % ≥ Q30 | Intensity | Aligned (%) | Error Rate 100 cycle (%) |
|---|---|---|---|---|---|---|
| 0.7 um | 59 | 0.117/0.162 (0.052/0.121) | 97.68 | 375 ± 0 | 99.39 ± 0.00 | 0.53 ± 0.00 |
| 0.9 um | 49 | 0.094/0.115 (0.225/0.250) | 96.78 | 345 ± 0 | 99.33 ± 0.00 | 0.56 ± 0.00 |
| 1.1 um | 37 | 0.097/0.111 0.358/0.350 | 96.88 | 374 ± 0 | 99.43 ± 0.00 | 0.50 ± 0.00 |

The results demonstrate that CYTOP patterning is compatiable with Illumina SBS chemistry, and that the surface is robust to allow thousane of flow exchanges to complete 2×150 bps sequencing runs.

What is claimed is:

1. A method of preparing a patterned surface with gel-coated contours, comprising:
providing a solid support having a surface covered by a continuous hydrophobic coating layer, wherein the hydrophobic coating layer is in direct contact with the surface or the hydrophobic coating layer is in contact with the surface via a first adhesion promoting layer;
disposing a photoresist layer on the hydrophobic coating layer of the solid support;
developing the photoresist layer to form micro-scale or nano-scale contours on the surface separated by hydrophobic interstitial regions;
removing the remaining photoresist layer; and
depositing a layer of a gel material within the micro-scale or nano-scale contours, wherein the gel material is capable of covalently bonding to oligonucleotides.

2. The method of claim 1, further comprising etching off the hydrophobic coating layer in at least a portion of the micro-scale or nano-scale contours prior to depositing the gel material.

3. The method of claim 2, further comprising applying a binding material layer or a silane layer to the surface to cover at least a portion of the micro-scale or nano-scale contours free of the hydrophobic coating layer prior to depositing the layer of the gel material.

4. The method of claim 3, further comprising removing excess gel material such that the hydrophobic interstitial regions are substantially free of the gel material.

5. The method of claim 3, wherein the binding material or the silane layer comprises a norbornene derivatized silane.

6. The method of claim 1, wherein the hydrophobic coating layer comprises a fluorinated polymer, a perfluorinated polymer, or a silicon polymer, or a mixture thereof.

7. The method of claim 6, wherein the hydrophobic coating layer comprises an amorphous fluoropolymer, an amorphous fluoropolymer having a backbone structure

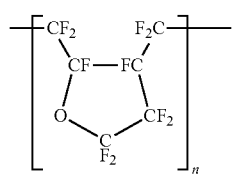

and end functional groups selected from the group consisting of carboxyl, silylated amide, and trifluoromethyl, a polytetrafluoroethylene, parylen, a fluorinated hydrocarbon, a fluoroacrylic copolymer, a fluorosilane, a plasma-deposited fluorocarbon, a silicon polymer, a polydimethylsiloxane, or a siloxane, or a mixture thereof.

8. The method of claim 1, wherein the first adhesion promoting layer comprises an amorphous fluoropolymer having a backbone structure

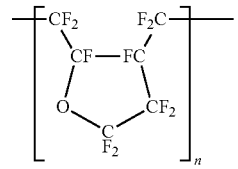

and carboxy end functional groups, (3-aminopropyl)trimethoxysilane (APTMS), or (3-aminopropyl)triethyoxysilane (APTES), or a combination thereof.

9. The method of claim 1, wherein the gel material comprises poly(N-(5-azidoacetamidylpentyl)acrylamide-co-acrylamide) (PAZAM).

10. A method for preparing a patterned surface for analytic applications, comprising:
providing a solid support having a surface covered by a continuous hydrophobic coating layer, wherein the hydrophobic coating layer is in direct contact with the surface or the hydrophobic coating layer is in contact with the surface via a first adhesion promoting layer;
disposing a photoresist layer and a second adhesion promoting layer on the hydrophobic coating layer of the solid support, wherein the photoresist layer is contact with the hydrophobic coating layer via the second adhesion promoting layer;
developing the photoresist layer to form micro-scale or nano-scale contours on the surface separated by hydrophobic interstitial regions;
etching off the hydrophobic coating layer in at least a portion of the micro-scale or nano-scale contours;
applying a binding material layer or a silane layer to the surface to cover at least a portion of the micro-scale or nano-scale contours free of hydrophobic coating layer; and
covalently attaching a gel material to the binding material layer or silane layer.

11. The method of claim 10, further comprising removing the remaining photoresist layer and the second adhesion promoting layer prior to applying the bonding material layer or the silane layer to the surface.

12. The method of claim 10, further comprising removing the remaining photoresist layer and the second adhesion promoting layer after covalently attached the gel material to the binding material layer or silane layer.

13. The method of claim 10, further comprising removing excess gel material such that the hydrophobic interstitial regions are substantially free of the gel material.

14. The method of claim 10, wherein the binding material or the silane layer comprises a norbornene derivatized silane.

15. The method of claim 10, wherein the hydrophobic coating layer comprises an amorphous fluoropolymer, an amorphous fluoropolymer having a backbone structure

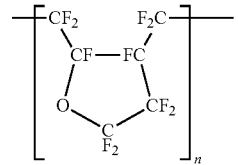

and end functional groups selected from the group consisting of carboxyl, silylated amide, and trifluoromethyl, a polytetrafluoroethylene, parylen, a fluorinated hydrocarbon, a fluoroacrylic copolymer, a fluorosilane, a plasma-deposited fluorocarbon, a silicon polymer, a polydimethylsiloxane, or a siloxane, or a mixture thereof.

16. The method of claim 10, wherein the first adhesion promoting layer comprises an amorphous fluoropolymer having a backbone structure

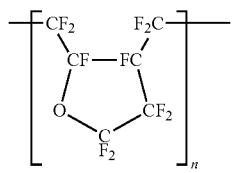

and carboxy end functional groups, (3-aminopropyl) trimethoxysilane (APTMS), or (3-aminopropyl)triethyoxysilane (APTES), or a combination thereof.

17. The method of claim 10, wherein the second adhesion promoting layer comprises one or more fluorinated surfactants.

18. The method of claim 10, wherein the gel material comprises poly(N-(5-azidoacetamidylpentyl)acrylamide-co-acrylamide) (PAZAM).

19. A method of preparing an array of polynucleotides, comprising
providing a solid support comprising a patterned surface comprising microscale or nanoscale contours coated with a gel material capable of covalently bonding to oligonucleotides, the patterned surface is prepared by the method of claim 10; and
covalently attaching a plurality of first oligonucleotides and a plurality of second oligonucleotides to the gel material.

20. The method of claim 19, further comprising contacting the plurality of first oligonucleotides attached to the polymer coating with templates to be amplified, each template comprising at the 3' end a sequence capable of hybridizing to the first oligonucleotides and at the 5' end a sequence the complement of which is capable of hybridizing to the second oligonucleotides.

21. The method of claim 20, further comprising amplifying the templates using the first oligonucleotides and the second oligonucleotides, thereby generating a clustered array of polynucleotides.

* * * * *

UNITED STATES PATENT AND TRADEMARK OFFICE
CERTIFICATE OF CORRECTION

PATENT NO. : 11,332,788 B2
APPLICATION NO. : 17/153379
DATED : May 17, 2022
INVENTOR(S) : Yir-Shyuan Wu et al.

It is certified that error appears in the above-identified patent and that said Letters Patent is hereby corrected as shown below:

In the Drawings

Sheet 7 of 19 (FIG. 7), Line 3, delete "Suflon" and insert -- Surflon --.

Sheet 8 of 19 (FIG. 8A), Line 3, delete "Suflon" and insert -- Surflon --.

In the Specification

Column 5, Line 48, delete "parylen" and insert -- parylene --.

Column 6, Line 2, delete "triethyoxysilane" and insert -- triethoxysilane --.

Column 9, Line 51, delete "parylen," and insert -- parylene, --.

Column 24, Line 67, delete "51805" and insert -- S1805 --.

Column 25, Line 28, delete "Suflon" and insert -- Surflon --.

Column 25, Line 28, delete "5651" and insert -- S651 --.

Column 25, Line 52, delete "Suflon-" and insert -- Surflon- --.

In the Claims

Column 27, Line 64, Claim 7, delete "parylen" and insert -- parylene --.

Column 28, Lines 14-15 (Approx.), Claim 8, delete "triethyoxysilane" and insert -- triethoxysilane --.

Column 28, Line 28, Claim 10, after "is" insert -- in --.

Signed and Sealed this
Twenty-second Day of November, 2022

*Katherine Kelly Vidal*
Katherine Kelly Vidal
*Director of the United States Patent and Trademark Office*

CERTIFICATE OF CORRECTION (continued)
U.S. Pat. No. 11,332,788 B2

Column 29, Line 3, Claim 15, delete "parylen" and insert -- parylene --.

Column 29, Lines 21-22 (approx.), Claim 16, delete "triethyoxysilane" and insert -- triethoxysilane --.